(12) United States Patent
Mylari

(10) Patent No.: US 6,544,998 B2
(45) Date of Patent: Apr. 8, 2003

(54) COMBINATION OF GABA AGONISTS AND SORBITOL DEHYDROGENASE INHIBITORS

(75) Inventor: Banavara L. Mylari, Waterford, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/997,038

(22) Filed: Nov. 29, 2001

(65) Prior Publication Data

US 2002/0091128 A1 Jul. 11, 2002

Related U.S. Application Data

(60) Provisional application No. 60/250,069, filed on Nov. 30, 2001.

(51) Int. Cl.[7] .................. A61K 31/505; A61K 31/55; A61K 31/535; A61K 31/425; A61K 31/415

(52) U.S. Cl. ............... 514/256; 514/212.01; 514/228.8; 514/367; 514/385; 514/386; 514/461; 514/473; 514/557; 514/620; 514/866

(58) Field of Search ............... 514/256, 212.01, 514/228.8, 367, 385, 386, 461, 473, 557, 620, 866

(56) References Cited

U.S. PATENT DOCUMENTS

| | | | |
|---|---|---|---|
| 2,409,754 A | 10/1946 | Henze | 260/309.5 |
| 3,242,190 A | 3/1966 | Hafliger et al. | 260/307 |
| 3,471,548 A | 10/1969 | Keberle et al. | 260/471 |
| 3,960,927 A | 6/1976 | Metcalf et al. | 260/471 A |
| 4,024,175 A * | 5/1977 | Satzinger et al. | 260/468 |
| 4,094,992 A * | 6/1978 | Kaplan et al. | 424/324 |
| 4,370,338 A * | 1/1983 | Mizoule | 424/270 |
| 4,513,006 A | 4/1985 | Maryanoff | 514/23 |
| 4,602,017 A | 7/1986 | Sawyer et al. | 514/242 |
| 5,010,090 A | 4/1991 | Gronvald et al. | 514/326 |
| 5,728,704 A * | 3/1998 | Mylari et al. | 514/256 |
| 5,866,578 A * | 2/1999 | Mylari et al. | 514/256 |
| 6,028,214 A | 2/2000 | Silverman et al. | 560/188 |
| 6,294,538 B1 * | 9/2001 | Mylari | 514/252.14 |
| 6,350,769 B1 * | 2/2002 | Kaufman et al. | 514/380 |

FOREIGN PATENT DOCUMENTS

WO    WO 0059510    10/2000    ......... A61K/31/505

* cited by examiner

*Primary Examiner*—Kevin E. Weddington
(74) *Attorney, Agent, or Firm*—Peter C. Richardson; Gregg C. Benson; Robert T. Ronau

(57) ABSTRACT

This invention relates to pharmaceutical compositions comprising combinations of a GABA agonist, a prodrug thereof or a pharmaceutically acceptable salt of said GABA agonist or said prodrug and a SDI, a prodrug thereof or a pharmaceutically acceptable salt of said SDI or said prodrug, kits containing such combinations and methods of using such combinations to treat mammals, including humans, suffering from diabetic complications such as diabetic neuropathy, diabetic nephropathy, diabetic cardiomyopathy, diabetic retinopathy, diabetic microangiopathy, diabetic macroangiopathy, cataracts or foot ulcers.

13 Claims, No Drawings

COMBINATION OF GABA AGONISTS AND SORBITOL DEHYDROGENASE INHIBITORS

CROSS-REFERENCE TO RELATED APPLICATIONS

The present application is a U.S. non-provisional application. This application claims the benefit of U.S. Pat. No. 60/250,069 filed on Nov. 30, 2001, under 35 USC 119(e).

FIELD OF THE INVENTION

This invention relates to pharmaceutical combinations of a γ-aminobutyric acid (GABA) agonist, a prodrug thereof or a pharmaceutically acceptable salt of said GABA agonist or said prodrug and a sorbitol dehydrogenase inhibitor (SDI), a prodrug thereof or a pharmaceutically acceptable salt of said SDI or said prodrug, kits containing such combinations and methods of using such combinations to treat mammals, including humans, suffering from diabetic complications such as, inter alia, diabetic neuropathy, diabetic nephropathy, diabetic cardiomyopathy, diabetic retinopathy, diabetic microangiopathy, diabetic macroangiopathy, cataracts or foot ulcers. This invention also relates to additive and synergistic combinations of a GABA agonist, a prodrug thereof or a pharmaceutically acceptable salt of said GABA agonist or said prodrug and a SDI, a prodrug thereof or a pharmaceutically acceptable salt of said SDI or said prodrug, whereby those additive and synergistic combinations are useful in treating mammals, including humans, suffering from diabetic complications such as, inter alia, diabetic neuropathy, diabetic nephropathy, diabetic cardiomyopathy, diabetic retinopathy, diabetic microangiopathy, diabetic macroangiopathy, cataracts or foot ulcers.

BACKGROUND OF THE INVENTION

GABA is the major inhibitory neurotransmitter in the mammalian central nervous system. Its receptors have been divided into two main types. The more prominent GABA receptor subtype, the $GABA_A$ receptor, is a ligand-gated $Cl^{31}$ ion channel that is opened after release of GABA from presynaptic neurons. A second receptor, the $GABA_B$ receptor, is a member of the G protein-coupled receptor family coupled both to biochemical pathways and to regulation of ion channels. (Goodman and Gilman's The Pharmacological Basis of Therapeutics, McGraw-Hill, New York, N. Y., $9^{th}$ Edition, (1996).

By gating negative chloride ($Cl^{31}$) ions into the interior of cells, GABA inhibits the presynaptic release of neurotransmitter due to a positive voltage polarization pulse. Such inhibition is extremely common: GABA receptors can be found in 60–80% of central nervous system neurons. Subtypes of GABA receptors can be activated by the mushroom toxin muscimol (at $GABA_A$) as well as the antispasmodic amino acid baclofen ($GABA_B$). These compounds directly mimic the action of GABA at the receptor. Allosteric facilitation of GABA receptors occurs at several distinct sites; the compounds which bind there are used as sedatives and anxiolytics. Progabide is a prodrug which decomposes to GABA after crossing the blood/brain barrier into the central nervous system. Vigabatrin (gamma-vinyl-GABA) promotes binding of GABA by inhibiting GABA-aminotransferase (GABA-T), the enzyme responsible for degrading GABA in the synapse.

GABA agonists well known in the art include muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®) and analogs, derivatives, prodrugs and pharmaceutically acceptable salts of those GABA agonists. It will be recognized by those skilled in the art in light of this disclosure that other GABA agonists are also useful in the combinations, pharmaceutical compositions, methods and kits of this invention. GABA agonists have been disclosed to be useful in antiseizure therapy for central nervous system disorders such as epilepsy, Huntington's chorea, cerebral ischemia, Parkinson's disease, tardive dyskinesia and spasticity. GABA agonists have also been disclosed to be useful as antidepressants, anxiolytics and antipsychotics. Further, GABA agonists have been disclosed to have utility in the treatment of pain.

S. Ao et al., *Metabolism*, 40, 77–87 (1991) have shown that significant functional improvement in the nerves of diabetic rats (based on nerve conduction velocity) occurs when nerve fructose levels are pharmacologically lowered, and that such improvement correlates more closely with the lowering of nerve fructose than the lowering of nerve sorbitol. Similar results were reported by N. E. Cameron and M. A. Cotter, *Diabetic Medicine, 8,* Suppl. 1, 35A-36A (1991). In both of these cases, lowering of nerve fructose was achieved using relatively high does of aldose reductase inhibitors, which inhibit the formation of sorbitol, a precursor of fructose, from glucose via the enzyme aldose reductase.

Commonly assigned U.S. Pat. Nos. 5,728,704 and 5,866,578, which are hereby incorporated by reference, each disclose compounds of the Formula A,

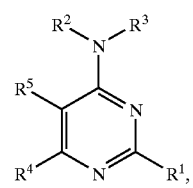

A wherein $R^1$ through $R^5$ in the compound of Formula A are defined as disclosed therein. Further, U.S. Pat. No. 5,728,704 discloses that sorbitol dehydrogenase compounds have utility in the treatment of diabetic complications.

Commonly assigned International Patent Application Publication Number WO00/59510, which is incorporated herein by reference, discloses compounds of the formula

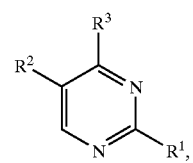

I wherein $R^1$ through $R^3$ in the compound of Formula I are defined as disclosed therein. That application discloses that the compounds of Formula I have utility in the treatment of diabetic complications.

SUMMARY OF THE INVENTION

This invention is directed to pharmaceutical compositions comprising:

a. an amount of a GABA agonist, a prodrug thereof or a pharmaceutically acceptable salt of said GABA agonist or said prodrug;

b. an amount of a SDI, a prodrug thereof or a pharmaceutically acceptable salt of said SDI or said prodrug; and, optionally, c. a pharmaceutically acceptable vehicle, carrier or diluent.

This invention is also directed to kits for achieving a therapeutic effect in a mammal comprising:

a. an amount of a GABA agonist, a prodrug thereof or a pharmaceutically acceptable salt of said GABA agonist or said prodrug and a pharmaceutically acceptable vehicle, carrier or diluent in a first unit dosage form;

b. an amount of a SDI, a prodrug thereof or a pharmaceutically acceptable salt of said SDI or said prodrug and a pharmaceutically acceptable vehicle, carrier or diluent in a second unit dosage form; and c. a container.

This invention is also directed to methods for treating a mammal in need of therapeutic treatment comprising administering to said mammal (a) an amount of a first compound, said first compound being a GABA agonist, a prodrug thereof or a pharmaceutically acceptable salt of said GABA agonist or said prodrug; and (b) an amount of a second compound, said second compound being a SDI, a prodrug thereof or a pharmaceutically acceptable salt of said SDI or said prodrug;

wherein said first compound and said second compound are each optionally and independently administered together with a pharmaceutically acceptable vehicle, carrier or diluent.

This invention is also directed to methods for treating a mammal in need of therapeutic treatment comprising administering to said mammal a pharmaceutical composition comprising (a) an amount of a first compound, said first compound being a GABA agonist, a prodrug thereof or a pharmaceutically acceptable salt of said GABA agonist or said prodrug; and (b) an amount of a second compound, said second compound being a SDI, a prodrug thereof or a pharmaceutically acceptable salt of said SDI or said prodrug; and, optionally, (c) a pharmaceutically acceptable vehicle, carrier or diluent.

The methods of this invention include therapeutic treatment of diabetic complications. Diabetic complications which may be treated by the methods of this invention include, inter alia, diabetic neuropathy, diabetic nephropathy, diabetic cardiomyopathy, diabetic retinopathy, diabetic microangiopathy, diabetic macroangiopathy, cataracts and foot ulcers. Humans are especially preferred mammals which are treated by the methods of this invention.

Preferred SDIs for use in the combinations, pharmaceutical compositions, methods and kits of this invention are compounds of Formula I,

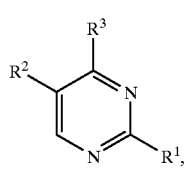

prodrugs thereof and pharmaceutically acceptable salts of said compounds and said prodrugs, wherein:

$R^1$ is formyl, acetyl, propionyl, carbamoyl or —C(OH)$R^4R^5$;

$R^4$ and $R^5$ are each independently hydrogen, methyl, ethyl or hydroxy-$(C_1-C_3)$alkyl;

$R^2$ is hydrogen, $(C_1-C_4)$alkyl or $(C_1-C_4)$alkoxy;

$R^3$ is a radical of the formula

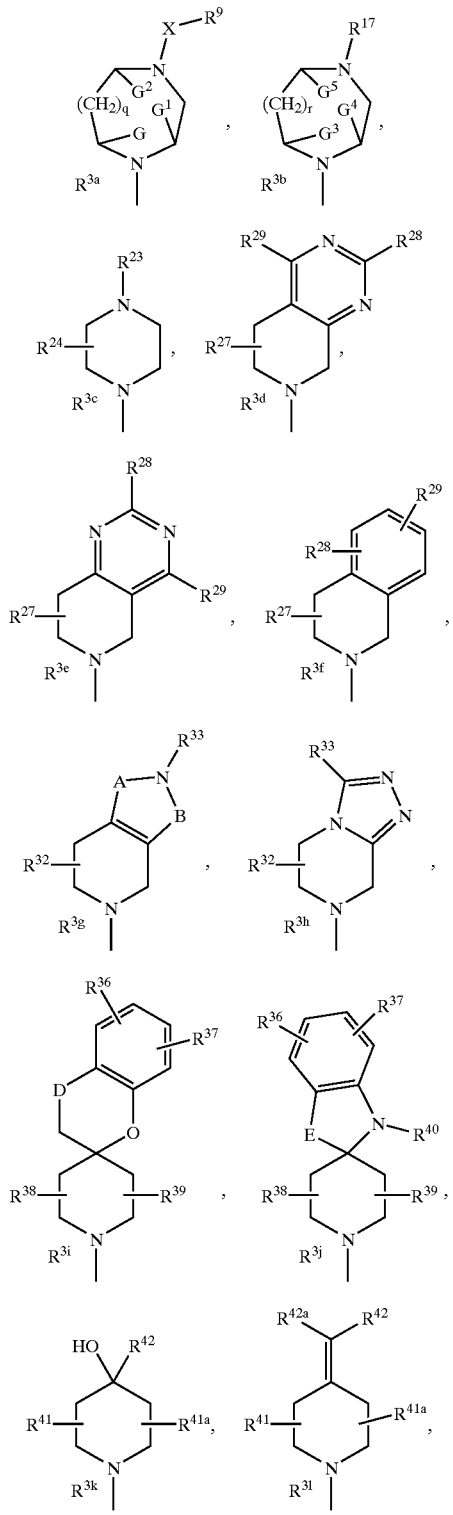

-continued

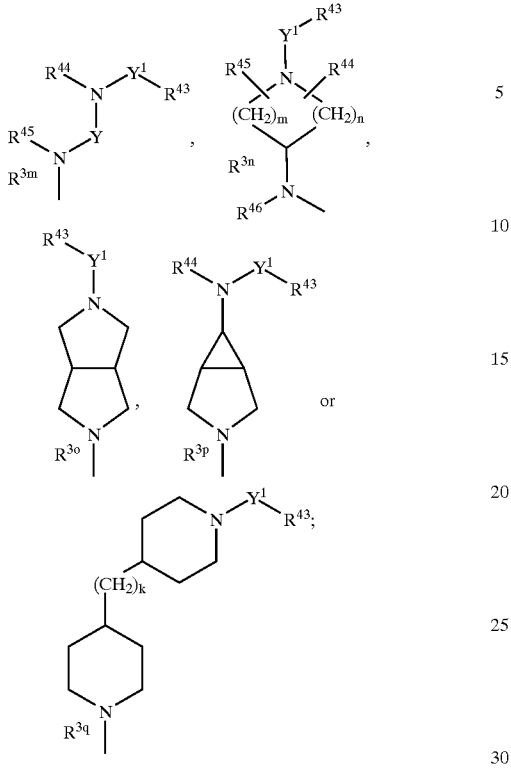

wherein said radical of formula $R^{3a}$ is additionally substituted on the ring by $R^6$, $R^7$ and $R^8$;
said radical of formula $R^{3b}$ is additionally substituted on the ring by $R^{18}$, $R^{19}$ and $R^{20}$; G, $G^1$ and $G^2$ are taken separately and are each hydrogen and $R^6$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; $R^7$ and $R^8$ are each independently hydrogen or $(C_1-C_4)$alkyl; or
$G^1$ and $G^2$ are taken together and are $(C_1-C_3)$alkylene and $R^6$, $R^7$, $R^8$ and $G^2$ are hydrogen; or
$G^1$ and $G^2$ are taken together and are $(C_1-C_3)$alkylene and $R^6$, $R^7$, $R^8$ and G are hydrogen;
q is 0 or 1;
X is a covalent bond, —(C=NR$^{10}$)—, oxycarbonyl, vinylenylcarbonyl, oxy$(C_1-C_4)$alkylenylcarbonyl, $(C_1-C_4)$alkylenylcarbonyl, $(C_3-C_4)$alkenylcarbonyl, thio$(C_1-C_4)$alkylenylcarbonyl, vinylenylsulfonyl, sulfinyl-$(C_1-C_4)$alkylenylcarbonyl, sulfonyl-$(C_1-C_4)$alkylenylcarbonyl or carbonyl$(C_0-C_4)$alkylenylcarbonyl; wherein said oxy$(C_1-C_4)$alkylenylcarbonyl, $(C_1-C_4)$alkylenylcarbonyl, $(C_3-C_4)$alkenylcarbonyl and thio$(C_1-C_4)$alkylenylcarbonyl in the definition of X are each optionally and independently substituted with up to two $(C_1-C_4)$alkyl, benzyl or Ar; said vinylenylsulfonyl and said vinylenylcarbonyl in the definition of X are optionally substituted independently on one or two vinylenyl carbons with $(C_1-C_4)$alkyl, benzyl or Ar; and said carbonyl$(C_0-C_4)$alkylenylcarbonyl in the definition of X is optionally substituted independently with up to three $(C_1-C_4)$alkyl, benzyl or Ar;
$R^{10}$ is hydrogen or $(C_1-C_4)$alkyl;
$R^9$ is $(C_3-C_7)$cycloalkyl, Ar$^1$—$(C_0-C_3)$alkylenyl or $(C_1-C_6)$alkyl optionally substituted with up to five fluoro; provided that when q=0 and X is a covalent bond, oxycarbonyl or $(C_1-C_4)$alkylenylcarbonyl, then $R^9$ is not $(C_1-C_6)$alkyl;
Ar and Ar$^1$ are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur;
Ar and Ar$^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from $R^{11}$, $R^{12}$, $R^{13}$ and $R^{14}$;
wherein $R^{11}$, $R^{12}$, $R^{13}$ and $R^{14}$ are each taken separately and are each independently halo, formyl, $(C_1-C_6)$alkoxycarbonyl, $(C_1-C_6)$alkylenyloxycarbonyl, $(C_1-C_4)$alkoxy-$(C_1-C_4)$alkyl, C(OH)R$^{15}$R$^{16}$, naphthyl, phenyl, imidazolyl, pyridyl, triazolyl, morpholinyl, $(C_0-C_4)$alkylsulfamoyl, N-$(C_0-C_4)$alkylcarbamoyl, N,N-di-$(C_1-C_4)$alkylcarbamoyl, N-phenylcarbamoyl, N-$(C_1-C_4)$alkyl-N-phenylcarbamoyl, N,N-diphenyl carbamoyl, $(C_1-C_4)$alkylcarbonylamido, $(C_3-C_7)$cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-$(C_1-C_4)$alkyl-3,8-diaza[3.2.1]bicyclooctyl, 3,5-dioxo-1,2,4-triazinyl, phenoxy, thiophenoxy, $(C_1-C_4)$alkylsulfanyl, $(C_1-C_4)$alkylsulfonyl, $(C_1-C_4)$alkylsulfonyl, $(C_3-C_7)$cycloalkyl, $(C_1-C_4)$alkyl optionally substituted with up to five fluoro or $(C_1-C_4)$alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1-C_4)$alkyl; said pyrrolidinyl in the definition of $R^{11}$, $R^{12}$, $R^{13}$ and $R^{14}$ is optionally substituted with up to two substituents independently selected from hydroxy, hydroxy-$(C_1-C_3)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1-C_4)$alkoxy-$(C_1-C_4)$alkyl, hydroxy-$(C_1-C_3)$alkyl, phenyl, pyridyl, $(C_0-C_4)$alkylsulfamoyl, $(C_1-C_4)$alkyl optionally substituted with up to five fluoro and $(C_1-C_4)$alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2-C_3)$alkyl or $(C_1-C_4)$alkyl optionally substituted with up to five fluoro; and said phenyl and pyridyl which are optionally substituted on piperazine in the definition of $R^{11}$, $R^{12}$, $R^{13}$ and $R^4$ are optionally substituted with up to three hydroxy, halo, hydroxy-$(C_1-C_4)$alkyl, $(C_1-C_4)$alkoxy-$(C_1-C_4)$alkyl, $(C_0-C_4)$alkyl optionally substituted with up to five fluoro and $(C_1-C_4)$alkoxy optionally substituted with up to five fluoro; or $R_{11}$ and $R^{12}$ are taken together on adjacent carbon atoms and are —$CH_2OC(CH_3)_2OCH_2$— or —O—$(CH_2)_p$—O—, and $R^{13}$ and $R^{14}$ are taken separately and are each independently hydrogen or $(C_1-C_4)$alkyl;

p is 1, 2 or 3;

$R^{15}$ and $R^{16}$ are taken separately and are each independently hydrogen, $(C_1-C_4)$alkyl optionally substituted with up to five fluoro; or $R^{15}$ and $R^{16}$ are taken separately and $R^{15}$ is hydrogen and $R^{16}$ is $(C_3-C_6)$cycloalkyl, hydroxy-$(C_1-C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3-C_6)$alkylene;

$G^3$, $G^4$ and $G^5$ are taken separately and are each hydrogen; r is 0; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently $(C_1-C_4)$alkyl; or $G^3$, $G^4$ and $G^5$ are taken separately and are each hydrogen; r is 1; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$ wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently hydrogen or $(C_1-C_4)$alkyl;
or $G^3$ and $G^4$ are taken together and are $(C_1-C_3)$alkylene; r is 0 or 1; and $R^{18}$, $R^{19}$, $R^{20\ and\ G5}$ are hydrogen; or $G^4$ and $G^5$ are taken together and are $(C_1-C_3)$alkylene; r is 0 or 1; and $R^{18}$, $R^{19}$, $R^{20\ and\ G3}$ are hydrogen;

$R^{17}$ is $SO_2NR^{21}R^{22}$, $CONR^2R^{22}$, $(C_1-C_6)$alkoxycarbonyl, $(C_1-C_6)$alkycarbonyl, $Ar^2$-carbonyl, $(C_1-C_6)$alkylsulfonyl, $(C_1-C_6)$alkylsulfinyl, $Ar^2$-sulfonyl, $Ar^2$-sufinyl and $(C_1-C_6)$alkyl;

$R^{21}$ and $R^{22}$ are taken separately and are each independently selected from hydrogen, $(C_1-C_6)$alkyl, $(C_3-C_7)$cycloalkyl and $Ar^2$—$(C_0-C_4)$alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrrolidinyl, piperidinyl, azepinyl in the definition of $R^{21}$ and $R^{22}$ are optionally substituted independently with up to two substituents independently selected from hydroxy, amino, hydroxy-$(C_1-C_4)$alkyl, $(C_1-C_4)$alkoxy-$(C_1-C_4)$alkyl, $(C_1-C_4)$alkyl optional substituted with up to five fluoro and $(C_1-C_4)$alkoxy optionally substituted with up to five fluoro; said morpholinyl in the definition of $R^{21}$ and $R^{22}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{21}$ and $R^{22}$ is optionally substituted independently with up to three substituents independently selected from phenyl, pyridyl, $(C_1-C_4)$alkoxycarbonyl and $(C_1-C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$ alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

$Ar^2$ is independently defined as set forth for Ar and $Ar^1$ above;

said $Ar^2$ is optionally independently substituted as set forth for Ar and $Ar^1$ above;

$R^{23}CONR^{25}R^{26}$ or $SO^2OR^{25}R^{26}$ wherein $R^{25}$ is hydrogen $(C_1-C_4)$alkyl or $Ar^3$—$(C_0-C_4)$alkylenyl and $R^{26}$ is $Ar^3$—$(C_0-C_4)$alkylenyl; provided that when $Ar^3$ is phenyl, naphthyl or biphenyl, then $R^{23}$ cannot be $CONR^{25}R^{26}$ where $R^{25}$ is hydrogen or $Ar^3$ and $R^{26}$ is $Ar^3$;

$R^{24}$ is hydrogen, $(C_1-C_4)$alkyl, $(C_1-C_4)$ alkoxycarbonyl, $(C_1-C_4)$alkoxy-$(C_1-C_4)$alkyl hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$ alkyl, $(C_1-C_4)$alkyl or $(C_1-C_4)$alkoxy, wherein said $(C_1-C_4)$alkyl in the definition of $R^6$ and said $(C_1-C_4)$ alkoxy in the definition of $R^6$ are optionally and independently substituted with up to five fluoro;

$Ar^3$ is independently defined as set forth for Ar and $Ar^1$ above;

said $Ar^3$ is optionally independently substituted as set forth for Ar and $Ar^1$ above;

$R^{27}$ is hydrogen or $(C_1-C_4)$alkyl;

$R^{28}$ and $R^{29}$ are each independently hydrogen, hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-$(C_1-C_4)$alkyl, $(C_1-C_4)$alkoxy-$(C_1-C_4)$ alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$ alkyl, $(C_1-C_4)$alkyl optionally substituted with up to five fluoro or $(C_1-C_4)$alkoxy optionally substituted with up to five fluoro;

$R^{30}$ and $R^{31}$ are each independently hydrogen, $(C_1-C_4)$ alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$ alkyl, $(C_1-C_4)$alkyl optionally substituted with up to five fluoro or $(C_1-C_4)$alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$ alkoxy optionally substituted with up to five fluoro; said indolinyl and piperazinyl in the definition of $R^{30}$ and $R^{31}$ are optionally substituted with up to three hydroxy, amino, hydroxy-$(C_1-C_4)$alkyl, $(C_1-C_4)$ alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

A is N optionally substituted with hydrogen or $(C_1-C_4)$ alkyl and B is carbonyl; or A is a carbonyl and B is N optionally substituted with hydrogen or $(C_1-C_4)$alkyl;

$R^{32}$ is hydrogen or $(C_1-C_4)$alkyl;

$R^{33}$ is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-$(C_1-C_4)$alkyl, $(C_1-C_4)$alkoxy-$(C_1-C_4)$alkyl, $(C_1-C_4)$alky optionally substituted with up to five fluoro or $(C_1-C_4)$ alkoxy optionally substituted with up to five fluoro;

$R^{34}$ and $R^{35}$ are each independently hydrogen, $(C_1-C_4$ alkyl), phenyl or phenylsulfonyl; said phenyl and phenylsulfonyl in the definition of $R^{34}$ and $R^{35}$ are optionally substituted with up to three halo, hydroxy, $(C_1-C_4)$alkyl optionally substituted with up to five fluoro or $(C_1-C_4)$alkoxy optionally substituted with up to five fluoro;

D is CO, CHOH or $CH_2$;

E is O, NH or S;

$R^{36}$ and $R^{37}$ are taken separately and are each independently hydrogen, halo, cyano, hydroxy, amino, $(C_1-C_6)$alkylamino, di-$(C_1-C_6)$alkylamino, pyrrolidino, piperidino, morpholino, $(C_1-C_4)$alkoxy-$(C_1-C_4)$alkyl, hydroxy-$(C_1-C_4)$alkyl, $Ar^4$, $(C_1-C_4)$ alkyl optionally substituted with up to five fluoro or $(C_1-C_4)$alkoxy optionally substituted with up to five fluoro;

$R^{38}$, $R^{39}$ and $R^{40}$ are each independently hydrogen or $(C_1-C_4)$-alkyl;

$Ar^4$ is phenyl, furanyl, thienyl, pyridyl, pyrimidyl, pyrazinyl or pyridazinyl; said $Ar^4$ being optionally substituted with up to three hydroxy, $(C_1-C_4)$alkoxy-$(C_1-C_4)$alkyl, halo, hydroxy-$(C_1-C_4)$alkyl, $(C_1-C_4)$ alkyl optionally substituted with up to five fluoro or $(C_1-C_4)$alkoxy optionally substituted with up to five fluoro; or $R^{36}$ and $R^{37}$ are taken together on adjacent carbon atoms and are —O—$(CH_2)_t$—O—;

t is 1, 2 or 3;

Y is $(C_2-C_6)$alkylene;

$R^{44}$, $R^{45}$ and $R^{46}$ are each independently hydrogen or $(C_1-C_4)$alkyl;

m and n are each independently 1, 2 or 3, provided that the sum of m and n is 2, 3 or 4;

k is 0, 1, 2, 3 or 4;

$Y^1$ is a covalent bond, carbonyl, sulfonyl or oxycarbonyl;

$R^{43}$ is $(C_3-C_7)$cycloalkyl, $Ar^5$—$(C_0-C_4)$alkylenyl, $NR^{47}R^{48}$ or $(C_1-C_6)$alkyl optionally substituted with one to five fluoro; provided that when $Y^1$ is a covalent bond or oxycarbonyl, then $R^{43}$ is not $NR^{47}R^{48}$;

$R^{47}$ and $R^{48}$ are taken separately and are each independently selected from hydrogen, $Ar^5$, $(C_1-C_6)$alkyl and $Ar^5$—$(C_0-C_4)$alkylenyl; or $R^{47}$ and $R^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said morpholinyl in the definition of $R^{47}$ and $R^{48}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$Ar^5$ is independently defined as set forth for Ar and $Ar^1$ above;

$Ar^5$ is optionally independently substituted as set forth for Ar and $Ar^1$ above;

$R^{42}$ and $R^{42a}$ are independently hydrogen, $(C_3-C_7)$cycloalkyl, $Ar^6$—$(C_0-C_3)$alkylenyl, $Ar^6$—$(C_2-C_4)$alkenyl, $Ar^6$-carbonyl or $(C_1-C_6)$alkyl optionally substituted with up to five fluoro;

$Ar^6$ is independently defined as set forth for Ar and $Ar^1$ above;

$Ar^6$ is optionally independently substituted as set forth for Ar and $Ar^1$ above; and $R^{41}$ and $R^{41a}$ are each independently hydrogen or $(C_1-C_4)$alkyl.

More preferred SDIs for use in the combinations, pharmaceutical compositions, methods and kits of this invention are compounds of Formula I of the immediately preceding paragraph, prodrugs thereof and pharmaceutically acceptable salts of said compounds and said prodrugs, wherein:

$R^1$ is $C(OH)R^4R^5$, where $R^4$ and $R^5$ are each independently hydrogen or methyl;

$R^2$ is hydrogen;

$R^3$ is

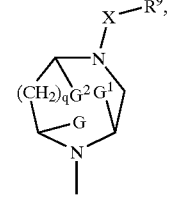

wherein said $R^3$ is substituted by $R^6$, $R^7$ or $R^8$;

G, $G^1$ and $G^2$ are taken separately and are each hydrogen and $R^6$ is hydrogen or $(C_1-C_4)$alkyl; $R^7$ and $R^8$ are each independently hydrogen or $(C_1-C_4)$alkyl; or G and $G^1$ are taken together and are $(C_1-C_3)$alkylene and $R^6$, $R^7$, $R^8$ and $G^2$ are hydrogen; or $G^1$ and $G^2$ are taken together and are $(C_1-C_3)$alkylene and $R^6$, $R^7$, $R^8$ and G are hydrogen;

q is 0 or 1;

X is a covalent bond, oxycarbonyl, vinylenylcarbonyl, oxy$(C_1-C_4)$alkylenylcarbonyl, thio$(C_1-C_4)$alkylenylcarbonyl or vinylenylsulfonyl; said vinylenylcarbonyl and said vinylenylsulfonyl in the definition of X are optionally substituted on one or two vinylenyl carbons with $(C_1-C_4)$alkyl, benzyl or Ar; said oxy$(C_1-C_4)$alkylenylcarbonyl and said thio$(C_1-C_4)$alkylenylcarbonyl in the definition of X are optionally substituted with up to two $(C_1-C_4)$alkyl, benzyl or Ar;

$R^9$ is $(C_3-C_7)$cycloalkyl, $Ar^1$—$(C_0-C_4)$alkylenyl or $(C_1-C_6)$alkyl optionally substituted with up to five fluoro;

$Ar^1$ is phenyl, naphthyl, pyridyl, pyrimidyl, pyrazinyl, pyridazinyl, triazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; and said Ar$^1$ is optionally substituted as set forth above in the definition of the variables of the compounds of Formula I.

Still more preferred SDIs for use in the combinations, pharmaceutical compositions, methods and kits of this invention are compounds of Formula I of the immediately preceding paragraph, prodrugs thereof and pharmaceutically acceptable salts of said compounds and said prodrugs, wherein:

X is a covalent bond, oxycarbonyl or vinylenylcarbonyl optionally substituted on one or two vinylenyl carbons with (C$_1$–C$_4$)alkyl, benzyl or Ar;

R$^9$ is Ar$^1$—(C$_0$–C$_4$)alkylenyl;

Ar$^1$ is phenyl, naphthyl, pyridyl, pyrimidyl, pyrazinyl, triazinyl, quinolyl, isoquinolyl, quinazolyl, quinoxalyl, furanyl, thienyl, indolyl, benzofuranyl, benzothienyl, benzoxazolyl, benzothiazolyl, furopyridyl, oxazolopyridyl, thiazolopyridyl, thienopyridyl, furopyrimidyl, thienopyrimidyl, oxazolopyrimidyl or thiazolopyrimidyl; and said Ar$^1$ is optionally substituted as set forth above in the definition of the variables of the compounds of Formula I.

Still more preferred SDIs for use in the combinations, pharmaceutical compositions, methods and kits of this invention are compounds of Formula I of the immediately preceding paragraph, prodrugs thereof and pharmaceutically acceptable salts of said compounds and said prodrugs, wherein:

R$^2$ is hydrogen;

R$^4$ is hydrogen or methyl;

R$^5$ is methyl;

G, G$^1$ and G$^2$ are hydrogen;

R$^6$ and R$^7$ are each independently hydrogen or methyl;

R$^8$ is hydrogen.

Particularly preferred SDIs for use in the combinations, pharmaceutical compositions, methods and kits of this invention include:

R-(4-{1'-[2-(1R-hydroxy-ethyl)-pyrimidin-4-yl]-[4,4'] bipiperidinyl-1-yl}-pyrimidin-2-yl)-ethanol;

furo[3,2-c]pyridin-2-yl-{4-[2-(1R-hydroxy-ethyl)-pyrimidin-4-yl]-3R,5S-dimethyl-piperazin-1-yl}-methanone;

(4-chloro-furo[3,2-c]pyridin-2-yl)-{4-[2-(1R-hydroxy-ethyl)-pyrimidin-4-yl]-3R,5-S-dimethyl-piperazin-1-yl}-methanone;

{4-[2-(1R-hydroxy-ethyl)-pyrimidin-4-yl]-3R,5S-dimethyl-piperazin-1-yl}-(4-pyrrolidin-1-yl-furo[3,2-c]pyridin-2-yl)-methanone;

{4-[2-(1R-hydroxy-ethyl)-pyrimidin-4-yl]-3R,5S-dimethyl-piperazin-1-yl}-(4-morpholin-4-yl-furo[3,2-c]pyridin-2-yl)-methanone;

{4-[2-(1R-hydroxy-ethyl)-pyrimidin-4-yl]-3R,5S-dimethyl-piperazin-1-yl}-imidazo[1,2-a]pyridin-2-yl-methanone;

furo[3,2-c]pyridin-2-yl-{4-[2-(1R-hydroxy-ethyl)-pyrimidin-4-yl]-2R,6S-dimethyl-piperazin-1-yl}-methanone;

4-[2-(1R-hydroxy-ethyl)-pyrimidin-4-yl]-2R,6S-dimethyl-piperazine-1-carboxylic acid pyridin-3-yl ester;

4-[2-(1R-hydroxy-ethyl)-pyrimidin-4-yl]-2R,6S-dimethyl-piperazine-1-carboxylic acid 2-methyl-pyridin-3-yl ester;

4-[2-(1R-hydroxy-ethyl)-pyrimidin-4-yl]-2R,6S-dimethyl-piperazine-1-carboxylic acid 5-chloro-pyridin-3-yl ester;

4-[2-(1R-hydroxy-ethyl)-pyrimidin-4-yl]-2R,6S-dimethyl-piperazine-1-carboxylic acid 6-methyl-pyridin-3-yl ester;

(E)-1-{4-[2-(1R-hydroxy-ethyl)-pyrimidin-4-yl]-2R,6S-dimethyl-piperazin-1-yl}-3-thiophen-2-yl-propenone;

1R-{4-[4-(4,6-dimethyl-pyrimidin-2-yl)-3R,5S-dimethyl-piperazin-1-yl]-pyrimidin-2yl}-ethanol;

1R-{4-[4-(4-methoxymethyl-6-methyl-pyrimidin-2-yl)-3R,5S-dimethyl-piperazin-1-yl]-pyrimidin-2-yl}-ethanol;

1R-{4-[4-(4-hydroxymethyl-6-methyl-pyrimidin-2-yl)-3R,5S-dimethyl-piperazin-1-yl]-pyrimidin-2-yl}-ethanol;

1R-(4-{3R,5S-dimethyl-4-[2-(4-methyl-piperazin-1-yl)-pyrimidin-4-yl]-piperazin-1-yl}-pyrimidin-2-yl)-ethanol;

1R-(4-{4-[2-(4-ethyl-piperazin-1-yl)-pyrimidin-4-yl]-3R,5S-dimethyl-piperazin-1-yl}-pyrimidin-2-yl)-ethanol;

1R-(4-{3R,5S-dimethyl-4-[2-(4-methyl-imidazol-1-yl)-pyrimidin-4-yl]-piperazin-1-yl}-pyrimidin-2-yl)-ethanol;

1R-(4-{3R,5S-dimethyl-4-[2-(2-methyl-imidazol-1-yl)-pyrimidin-4-yl]-piperazin-1-yl}pyrimidin-2-yl)-ethanol;

1R-(4-{4-[2-(2,4-dimethyl-imidazol-1-yl)-pyrimidin-4-yl]-3R,5S-dimethyl-piperazin-1-yl}-pyrimidin-2-yl)-ethanol;

1R-(4-{4-[2-(4-isopropyl-piperazin-1-yl)-pyrimidin-4-yl]-3R,5S-dimethyl-piperazin-1-yl}-pyrimidin-2-yl)-ethanol;

1R-(4-{3R,5S-dimethyl-4-[4-methyl-6-(4-methyl-piperazin-1-yl)-[1,3,5]triazin-2-yl]-piperazin-1-yl}-pyrimidin-2-yl)-ethanol;

1R-{4-[4-(4-methoxy-6-methyl-[1,3,5]triazin-2-yl)-3R,5S-dimethyl-piperazin-1-yl]-pyrimidin-2-yl}-ethanol;

1R-{-[4-(4,6-dimethoxy-[1,3,5]triazin-2-yl)-3R,5S-dimethyl-piperazin-1-yl]-pyrimidin-2-yl}-ethanol;

1R-{4-[4-(4-ethoxy-6-methyl-[1,3,5]triazin-2-yl)-3R,5S-dimethyl-piperazin-1-yl]-pyrimidin-2-yl}-ethanol;

1R-{4-[4-(4-isopropoxy-6-methyl-[1,3,5]triazin-2-yl)-3R,5S-dimethyl-piperazin-1-yl]-pyrimidin-2-yl}-ethanol;

1R-{4-[3R,5S-dimethyl-4-(4-phenyl-[1,3,5]triazin-2-yl)-piperazin-1-yl]-pyrimidin-2-yl}-ethanol;

1R-{4-[4-(4-hydroxymethyl-6-methoxy-[1,3,5]triazin-2-yl)-3R,5S-dimethyl-piperazin-1-yl]-pyrimidin-2-yl}-ethanol;

1R-{4-[4-(4-isopropoxy-6-methoxy-[1,3,5]triazin-2-yl)-3R,5S-dimethyl-piperazin-1-yl]-pyrimidin-2-yl}-ethanol;

1R-{4-[4-(4-isopropyl-[1,3,5]triazin-2-yl)-3R,5S-dimethyl-piperazin-1-yl]-pyrimidin-2-yl}-ethanol;

1R-{4-[4-(4-ethyl-6-methoxy-[1,3,5]triazin-2-yl)-3R,5S-dimethyl-piperazin-1-yl]-pyrimidin-2-yl}-ethanol;

1R-{4-[4-(4,6-dimethyl-pyrimidin-2-yl)-2R,6S-dimethyl-piperazin-1-yl]-pyrimidin-2-yl}-ethanol;

1R-{4-[4-(4-hydroxymethyl-6-methyl-pyrimidin-2-yl)-2R,6S-dimethyl-piperazin-1-yl]-pyrimidin-2-yl}-ethanol;

1R-{4-[2R,6S-dimethyl-4-(4-[1,2,4]triazol-1-yl-pyrimidin-2-yl)-piperazin-1-yl]pyrimidin-2-yl}-ethanol;

1R-{4-[4-(2,6-dimethyl-pyrimidin-4-yl)-2R,6S-dimethyl-piperazin-1-yl]-pyrimidin-2-yl}-ethanol;

1R-(4-{4-[2-(1R-hydroxy-ethyl)-pyrimidin-4-yl]-2R,6S-dimethyl-piperazin-1-yl}-pyrimidin-2-yl)-ethanol;

1R-{4-[4-(2-hydroxymethyl-6-methyl-pyrimidin-4-yl)-2R,6S-dimethyl-piperazin-1-yl]-pyrimidin-2-yl}-ethanol;

1R-(4-{4-[2-(1S-hydroxy-ethyl)-pyrimidin-4-yl]-2R,6S-dimethyl-piperazin-1-yl}-pyrimidin-2-yl)-ethanol;

1S-(4-{4-[2-(1R-hydroxy-ethyl)-pyrimidin-4-yl]-2R,6S-dimethyl-piperazin-1-yl}-pyrimidin-2-yl)-ethanol;

1-{4-[4-(2-acetyl-pyrimidin-4-yl)-2R,6S-dimethyl-piperazin-1-yl]-pyrimidin-2-yl}-ethanone;

1RS-(4-{4-[2-(1RS-hydroxy-ethyl)-pyrimidin-4-yl]-2R,6S-dimethyl-piperazin-1-yl}-pyrimidin-2-yl)-ethanol;

(4-{4-[2-(1R-hydroxy-ethyl)-pyrimidin-4-yl]-3R,5S-dimethyl-piperazin-1-yl}-pyrimidin-2-yl)-ethanone;

1R-{4-[2R,6S-dimethyl-4-(2-morpholin-4-yl-pyrimidin-4-yl)-piperazin-1-yl]-pyrimidin-2-yl}-ethanol;

1R-(4-{2R,6S-dimethyl-4-[2-(4-methyl-piperazin-1-yl)-pyrimidin-4-yl]-piperazin-1-yl }-pyrimidin-2-yl)-ethanol;

1R-{4-[2R,6S-dimethyl-4-(2-[1,2,4]triazol-1-yl-pyrimidin-4-yl)-piperazin-1-yl]-pyrimidin-2-yl}-ethanol;
1R-(4-{4-[2-(1R-hydroxy-ethyl)-pyrimidin-4-yl]-2R,6R-dimethyl-piperazin-1-yl}-pyrimidin-2-yl)-ethanol;
1R-(4-{4-[2-(4-ethyl-piperazin-1-yl)-pyrimidin-4-yl]-2R,6S-dimethyl-piperazin-1-yl}-pyrimidin-2-yl)-ethanol;
1R-(4-{2R,6S-dimethyl-4-[2-(4-methyl-imidazol-1-yl)-pyrimidin-4-yl]-piperazin-1-yl}-pyrimidin-2-yl)-ethanol;
1R-(4-{4-[2-(2,4-dimethyl-imidazol-1-yl)-pyrimidin-4-yl]-2R,6S-dimethyl-piperazin-1-yl}-pyrimidin-2-yl)-ethanol;
1R-{4-[2R,6S-dimethyl-4-(4-morpholin-4-yl-[1,3,5]triazin-2-yl)-piperazin-1-yl]-pyrimidin-2-yl}-ethanol;
1R-{4-[4-(4-methoxy-6-methyl-[1,3,5]triazin-2-yl)-2R,6S-dimethyl-piperazin-1-yl]-pyrimidin-2-yl}-ethanol;
1R-{4-[4-(4,6-dimethoxy-[1,3,5]triazin-2-yl)-2R,6S-dimethyl-piperazin-1-yl]-pyrimidin-2-yl}-ethanol;
1R-{4-[2R,6S-dimethyl-4-(4-phenyl-[1,3,5]triazin-2-yl)-piperazin-1-yl]-pyrimidin-2-yl}-ethanol;
1R-{4-[4-(4-hydroxymethyl-6-methyl-pyrimidin-2-y)-3S-methyl-piperazin-1-yl]-pyrimidin-2-yl}-ethanol;
1R-{4-[4-(2-hydroxymethyl-pyrimidin-4-yl)-3S-methyl-piperazin-1-yl]-pyrimidin-2-yl}-ethanol;
1R-{4-[4-(2-hydroxymethyl-6-methyl-pyrimidin-4-yl)-3S-methyl-piperazin-1-yl]-pyrimidin-2-yl}-ethanol;
1R-[4-(3S-methyl-4-oxazolo[5,4-b]pyridin-2-yl-piperazin-1-yl)-pyrimidin-2-yl]-ethanol;
1R-[4-(3S-methyl-4-oxazolo[4,5-b]pyridin-2-yl-piperazin-1-yl)-pyrimidin-2-yl]-ethanol;
1R-[4-(3S-methyl-4-quinoxalin-2-yl-piperazin-1-yl)-pyrimidin-2-yl]-ethanol;
1R-{4-[4-(4,6-dimethyl-[1,3,5]triazin-2-yl)-3R,5S-dimethyl-piperazin-1-yl]-pyrimidin-2-yl}-ethanol;
1R-{4-[3R,5S-dimethyl-4-(4-methyl-6-phenyl-[1,3,5]triazin-2-yl)-piperazin-1-yl]pyrimidin-2-yl}-ethanol;
1R-{4-[4-(4-cyclopropyl-[1,3,5]triazin-2-yl)-3R,5S-dimethyl-piperazin-1-yl]-pyrimidin-2-yl}-ethanol;
1R-{4-[4-(4-cyclopropyl-[1,3,5]triazin-2-yl)-2R,6S-dimethyl-piperazin-1-yl]-pyrimidin-2-yl}-ethanol;
1R-{4-[4-(4,6-dimethyl-[1,3,5]triazin-2-yl)-2R,6S-dimethyl-piperazin-1-yl]-pyrimidin-2-yl}-ethanol;
1R-{4-[4-(4-hydroxymethyl-6-phenyl-[1,3,5]triazin-2-yl)-2R,6S-dimethyl-piperazin-1-yl]-pyrimidin-2-yl}-ethanol;
1R-{4-[4-(4-methoxy-6-methoxymethyl-[1,3,5]triazin-2-yl)-2R,6S-dimethyl-piperazin-1-yl]-pyrimidin-2-yl}-ethanol;
1R-{4-[2R,6S-dimethyl-4-(4-methyl-[1,3,5]triazin-2-yl)-piperazin-1-yl]-pyrimidin-2-yl-ethanol;
1-{4-[4-(2-acetyl-pyrimidin-4-yl)-2R*,6S*-dimethyl-piperazin-1-yl]-pyrimidin-2-yl}-ethanone;
1-(-4-{4-[2-(1R-hydroxy-ethyl)-pyrimidin-4-yl]-2R,6S-dimethyl-piperazin-1-yl}-pyrimidin-2-yl)-ethanone;
1R-{4-[4-(4-methoxymethyl-6-phenyl-[1,3,5]-triazin-2-yl)-2R,6S-dimethyl-piperazin-1-yl]-pyrimidin-2-yl}-ethanol;
(4-{4-[2-(1R-hydroxy-ethyl)-pyrimidin-4-yl]-2R,5S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; prodrugs thereof and pharmaceutically acceptable salts of said compounds and said prodrugs.

More particularly preferred SDIs for use in the combinations, pharmaceutical compositions, methods and kits of this invention include:
1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-(4-{4-[2-(1S-hydroxy-ethyl)-pyrimidin-4-yl]-2R,6S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; 1-{4-[4-(2-acetyl-pyrimidin-4-yl)-2R,6S-dimethyl-piperazin-1-yl]-pyrimidin-2-yl}-ethanone; 1RS-(4-{4-[2-(1RS-hydroxy-ethyl)-pyrimidin-4-yl]-2R,6S-dimethyl-piperazin-1-yl}-pyrimidin-2-yl)-ethanol; (4-4-[2-(1R-hydroxy-ethyl)-pyrimidin-4-yl]-3R,5S-dimethyl-piperazin-1-yl]-pyrimidin-2-yl)-ethanone; 1R-{4-[2R,6S-dimethyl-4-(2-morpholin-4-yl-pyrimidin-4-yl)-piperazin-1-yl]-pyrimidin-2-yl}-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-{4-[2R,6S-dimethyl-4-(2-[1,2,4]triazol-1-yl-pyrimidin-4-yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; 1R-{4-[4-(4-cyclopropyl-[1,3,5]triazin-2-yl)-2R,6S-dimethyl-piperazin-1-yl]-pyrimidin-2-yl}-ethanol; 1R-{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-piperazin-1-yl]-pyrimidin-2-yl-ethanol; and 1R-(4-{4-[2-(2,4-dimethyl-imidazol-1-yl)-pyrimidin-4-yl]-2R,6S-dimethyl-piperazin-1-yl}-pyrimidin-2-yl)-ethanol; prodrugs thereof and pharmaceutically acceptable salts of said compounds and said prodrugs.

Preferred GABA agonists for use in the combinations, pharmaceutical compositions, methods and kits of this invention include: muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®), prodrugs thereof and pharmaceutically acceptable salts of said GABA agonists and said prodrugs.

More preferred GABA agonists for use in the combinations, pharmaceutical compositions, methods and kits of this invention include gabapentin, tiagabine, lamotrigine, phenytoin, carbamazepine, topiramate, pregabalin, prodrugs thereof and pharmaceutically acceptable salts of said GABA agonists and said prodrugs.

A particularly preferred GABA agonist for use in the combinations, pharmaceutical compositions, methods and kits of this invention is pregabalin, a prodrug thereof or a pharmaceutically acceptable salt of said pregabalin or said prodrug.

Another particularly preferred GABA agonist for use in the combinations, pharmaceutical compositions, methods and kits of this invention is gabapentin (Neurontin®), a prodrug thereof or a pharmaceutically acceptable salt of said gabapentin (Neurontin®) or said prodrug.

DETAILED DESCRIPTION OF THE INVENTION

The combinations of this invention comprise two active components: a GABA agonist, a prodrug thereof or a pharmaceutically acceptable salt of said GABA agonist or said prodrug and a SDI, a prodrug thereof or a pharmaceutically acceptable salt of said SDI or said prodrug. The combinations of this invention optionally include a pharmaceutically acceptable vehicle, carrier or diluent.

The first component of the combinations of this invention is a GABA agonist, a prodrug thereof or a pharmaceutically acceptable salt of said GABA agonist or said prodrug. The term "GABA", where used in the description and the appendant claims, is synonymous with the term "γ-aminobutyric acid." These terms are used interchangeably throughout the description and appendant claims The GABA agonists suitable for use herein include, but are not limited to, muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®), a prodrug thereof or a pharmaceutically acceptable salt of said GABA agonist or said prodrug. It will be recognized by those skilled in the art in light of this disclosure that other GABA agonists are also useful in the combinations, pharmaceutical compositions, methods and kits of this invention.

The structures of the preferred GABA agonists are set forth in Scheme I below.

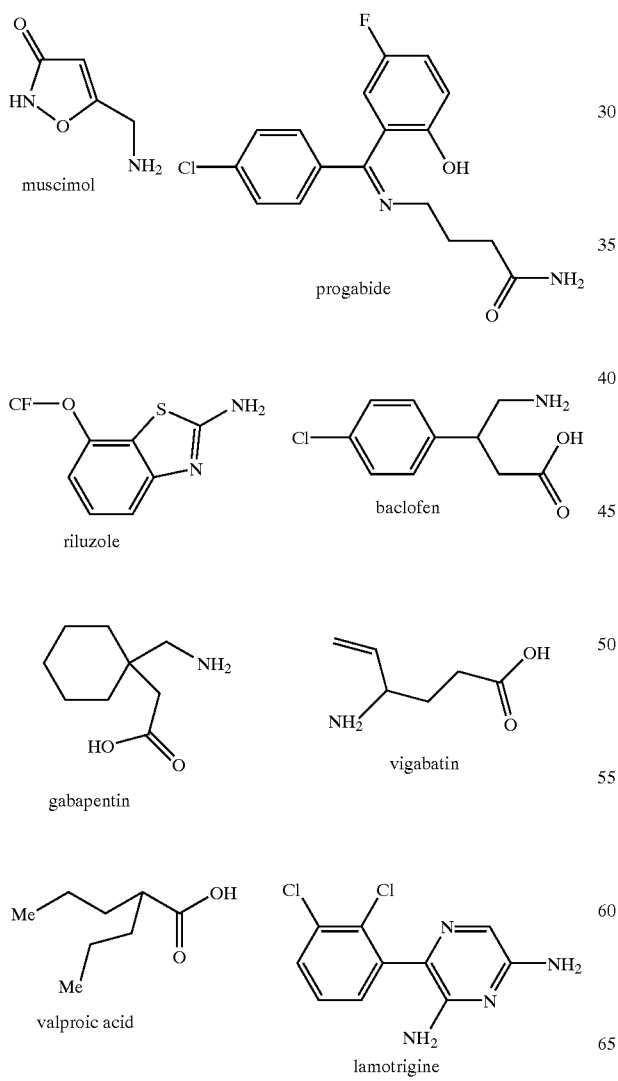

The GABA agonists disclosed herein are prepared by methods well known to those skilled in the art. Specifically, the following patents and patent applications, each of which is hereby incorporated herein by reference, exemplify GABA agonists which can be used in the combinations, pharmaceutical compositions, methods and kits of this invention, and refer to methods of preparaing those GABA agonists: U.S. Pat. No. 3,242,190 (specifically, muscimol); U.S. Pat. No. 4,094,992 (specifically, progabide); U.S. Pat. No. 4,370,338 (specifically, riluzole); U.S. Pat. No. 3,471,548 (specifically, baclofen); U.S. Pat. No. 4,024,175 (specifically, gabapentin); U.S. Pat. No. 3,960,927 (specifically, vigabatrin); U.S. Pat. No. 5,010,090 (specifically, tiagabine); U.S. Pat. No. 4,602,017 (specifically, lamotrigine); U.S. Pat. No. 6,028,214 (specifically, pregabalin); U.S. Pat. No. 2,409,754 (specifically, phenytoin) and U.S. Pat. No. 4,513,006 (specifically, topiramate). Valproic acid is prepared as disclosed in Carraz et al., Therapie, 1965, 20, 419.

Any SDI may be used as one of the active ingredients in the combinations, pharmaceutical compositions, methods and kits of the instant invention. Compounds of the Formula A, above, may be prepared as set forth in U.S. Pat. No. 5,728,704 and/or U.S. Pat. No. 5,866,578.

In general the SDIs of Formula I of this invention can be made by processes which include processes known in the chemical arts. SDIs of Formula I of this invention are prepared as set forth in International Patent Application Publication Number WO00/59510, which is incorporated herein by reference.

It will be recognized that certain of the GABA agonists and SDIs used in the pharmaceutical compositions, methods and kits of this invention contain either a free carboxylic acid or a free amine group as part of the chemical structure. Thus, this invention includes pharmaceutically acceptable salts of those carboxylic acids or amine groups. The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The pharmaceutically-acceptable cationic salts of GABA agonists or SDIs containing free carboxylic acids may be readily prepared by reacting the free acid form of the GABA agonists or SDIs with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (e.g., sodium or potassium ethylhexanoate, magnesium oleate), employlng a solvent (e.g., ethyl acetate) from which the desired cationic salt precipitates, or can be otherwise isolated by concentration and/or addition of a non-solvent.

The pharmaceutically acceptable acid addition salts of GABA agonists or SDIs containing free amine groups may be readily prepared by reacting the free base form of the GABA agonist or SDI with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The expression "prodrug" refers to compounds that are drug precursors which, following administration, release the drug in vivo via some chemical or physiological process (e.g., a prodrug on being brought to the physiological pH or through enzyme action is converted to the desired drug form). Both the GABA agonists and the SDIs used in the combinations, pharmaceutical compositions, methods and kits of this invention may be prepared as prodrugs. The preparation of prodrugs is straightforward and may be achieved using methods well known to those skilled in the art. All such prodrugs are within the scope of the combinations, pharmaceutical compositions, methods and kits of this invention.

The chemist of ordinary skill in the art will also recognize that certain compounds within the scope of this invention can exist in tautomeric form, i.e., that an equilibrium exists between two isomers which are in rapid equilibrium with each other. A common example of tautomerism is keto-enol tautomerism, i.e.,

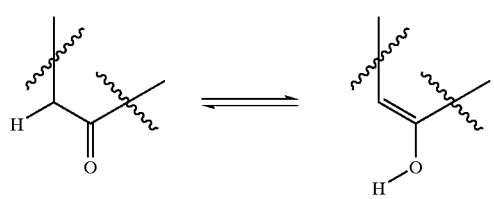

Examples of compounds which can exist as tautomers include hydroxypyridines, hydroxypyrimidines and hydroxyquinolines. Other examples will be recognized by those skilled in the art. All such tautomers and mixtures thereof are included in this invention.

The chemist of ordinary skill in the art will also recognize that certain compounds within the scope of this invention can exist in zwitterionic form, i.e., that certain compounds contain an amine portion and a carboxylic acid portion, which, depending upon the pH of the solution, may exist as a free amine and a free carboxylic acid or as a zwitterion in which the amine is protonated to form an ammonium ion and the carboxylic acid is deprotonated to form a carboxylate ion. All such zwitterions are included in this invention.

In addition, the GABA agonists, prodrugs thereof and pharmaceutically acceptable salts of said GABA agonists and said prodrugs used in the combinations of the instant invention may occur as hydrates or solvates. Further, the SDIs, prodrugs thereof and pharmaceutically acceptable salts of said SDIs and said prodrugs used in the combinations of the instant invention may also occur as hydrates or solvates. Said hydrates and solvates are also within the scope of the invention.

The sorbitol dehydrogenase inhibiting activity of the SDIs used in the combinations, pharmaceutical compositions, methods and kits of this invention may be determined according to procedures well known to those skilled in the art and particularly as set forth in commonly assigned International Patent Application Publication No. WO00/59510. Methods for determining the GABA agonist activity of the GABA agonists used in the combinations, pharmaceutical compositions, methods and kits of this invention are well known and may be achieved by following the procedures disclosed, for example, in Janssens de Verebeke, P. et al., Biochem. Pharmacol., 31, 2257–2261 (1982), Loscher, W., Biochem. Pharmacol., 31, 837–842, (1982) and/or Phillips, N. et al., Biochem. Pharmacol., 31, 2257–2261.

The above assays demonstrating the effectiveness of SDIs, prodrugs thereof and pharmaceutically acceptable acid addition salts of said SDIs and said prodrugs, and GABA agonists, prodrugs thereof and pharmaceutically acceptable salts of said GABA agonists and said prodrugs in the treatment of diabetic complications also provide a means whereby the activities of the compounds of this invention can be compared between themselves and with the activities of other known compounds. The results of these comparisons are useful for determining dosage levels in mammals, including humans, for the treatment of such diseases.

The effect of a pharmaceutical composition comprising a GABA agonist and a SDI of the present invention may be examined by using one or more of the published models of diabetic complications well known in the art. The pharmaceutical compositions of the present invention are particularly useful for the prevention of, reducing the development of, or reversal of, deficits in nerve function found in diabetic patients, and therefore are particularly useful in the treatment of diabetic neuropathy. This may be demonstrated, for example, by measuring markers such as nerve conduction velocity, nerve amplitude, quantitative sensory testing, autonomic function testing and morphometric changes. Studies analogous to those described in Diabetologia, 1992, Vol. 35, pages 12–18 and 1994, Vol. 37, pages 651–663 may be carried out.

In general, the SDIs used in the combinations, pharmaceutical compositions, methods and kits of this invention, and particularly the compounds of Formula I, and their pharmaceutically acceptable salts, will be administered at dosages between about 0.001 and about 100 mg/kg body weight of the subject to be treated per day, preferably from about 0.01 mg/kg to about 10 mg/kg, in single or divided doses. However, some variation in dosage will necessarily occur depending upon the condition of the subject being treated. The person responsible for administration will, in any event, determine the appropriate dose for the individual subject.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject. All doses set forth herein, and in the appendant claims, are daily doses.

In general, in accordance with this invention, the above GABA agonists used in the combinations, pharmaceutical compositions, methods and kits of this invention will be administered in a dosage amount of about 4 mg/kg body weight of the subject to be treated per day to about 60 mg/kg body weight of the subject to be treated per day, in single or divided doses. However, some variation in dosage will necessarily occur depending upon the condition of the subject being treated. The person responsible for administration will, in any event, determine the appropriate dose for the individual subject. In particular, when used as the GABA agonist in this invention, pregabalin will be dosed at about 300 mg to about 1200 mg per day; gabapentin will be dosed at about 600 mg to about 3600 mg per day.

It will be recognized by a skilled person that the free base form or other salt forms of the above GABA agonists and SDIs may be used in this invention. Calculation of the dosage amount for these other forms of the free base form or other salt forms of a particular GABA agonist or SDI is easily accomplished by performing a simple ratio relative to the molecular weights of the species involved.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifylng agents and/or suspending agents, as well as such diluents as water, ethanol, propylene glycol, glycerin and various like combinations thereof.

The combinations of this invention may also be administered in a controlled release formulation such as a slow release or a fast release formulation. Such controlled release formulations of the combinations of this invention may be prepared using methods well known to those skilled in the art. The method of administration will be determined by the attendant physician or other person skilled in the art after an evaluation of the subject's condition and requirements.

The combinations of this invention may also be administered in parenteral form. For parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art. For examples, see Remington: The Science and Practice of Pharmacy, Mack Publishing Company, Easton, Pa., 19th Edition (1995).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the condition or disease of the subject being treated.

The two different compounds of this invention can be co-administered simultaneously or sequentially in any order, or as a single pharmaceutical composition comprising a SDI and a GABA agonist as described above.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a SDI, a prodrug thereof or a pharmaceutically acceptable salt of said SDI or prodrug and a GABA agonist, a prodrug thereof or a pharmaceutically acceptable salt of said GABA agonist or prodrug. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applylng pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also, a daily dose of the SDI can consist of one tablet or capsule while a daily dose of the GABA agonist can consist of several tablets or capsules or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

It should be understood that the invention is not limited to the particular embodiments described herein, but that various changes and modifications may be made without departing from the spirit and scope of this novel concept as defined by the following claims.

What is claimed is:

1. A method for treating a diabetic complication in a mammal comprising administering to said mammal suffering from a diabetic complication
   (a) an amount of a first compound, said first compound being a GABA agonist, a prodrug thereof or a pharmaceutically acceptable salt of said GABA agonist or said prodrug; and
   (b) an amount of a second compound, said second compound being a sorbitol dehydrogenase inhibitor (SDI), a prodrug thereof or a pharmaceutically acceptable salt of said SDI or said prodrug.

2. A method of claim 1 wherein said GABA agonist, prodrug thereof or pharmaceutically acceptable salt of said GABA agonist or said prodrug and said SDI, prodrug thereof or pharmaceutically acceptable salt of said SDI or said prodrug are administered in a pharmaceutical composition additionally comprising a pharmaceutically acceptable vehicle, carrier or diluent.

3. A method of claim 1 wherein said diabetic complication is diabetic nephropathy, diabetic neuropathy, diabetic cardiomyopathy, diabetic retinopathy, foot ulcers, diabetic microangiopathy, diabetic macroangiopathy or cataracts.

4. A method of claim 3 wherein said diabetic complication is diabetic nephropathy.

5. A method of claim 3 wherein said diabetic complication is diabetic neuropathy.

6. A method of any one of claims 1–5 wherein said GABA agonist is muscimol, progabide, riluzole, baclofen, gabapentin, vigabatrin, valproic acid, tiagabine, lamotrigine, pregabalin, phenytoin, carbamazepine, topiramate, a prodrug thereof or a pharmaceutically acceptable salt of said GABA agonist or said prodrug.

7. A method of claim 6 wherein said GABA agonist is pregabalin, a prodrug thereof or a pharmaceutically acceptable salt of said pregabalin or said prodrug.

8. A method of claim 6 wherein said GABA agonist is gabapentin, a prodrug thereof or a pharmaceutically acceptable salt of said gabapentin or said prodrug.

9. A method of claim any one of claims 1–5 wherein said SDI is a compound of Formula I,

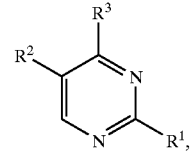

a prodrug thereof or a pharmaceutically acceptable salt of said compound or said prodrug, wherein:

$R^1$ is formyl, acetyl, propionyl, carbamoyl or —C(OH)$R^4R^5$;

$R^4$ and $R^5$ are each independently hydrogen, methyl, ethyl or hydroxy-$(C_1-C_3)$alkyl;

$R^2$ is hydrogen, $(C_1-C_4)$alkyl or $(C_1-C_4)$alkoxy;

$R^3$ is a radical of the formula

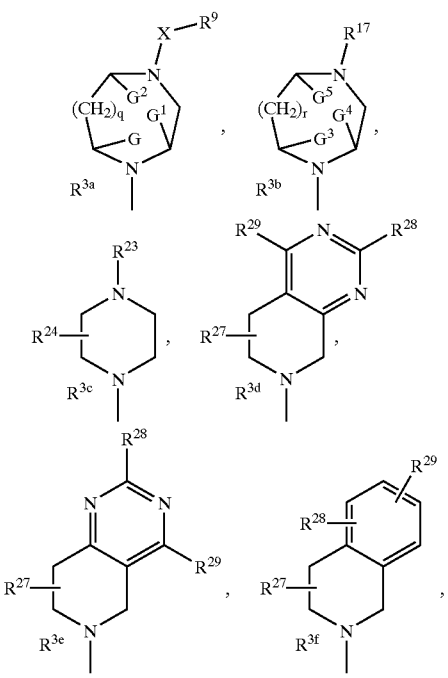

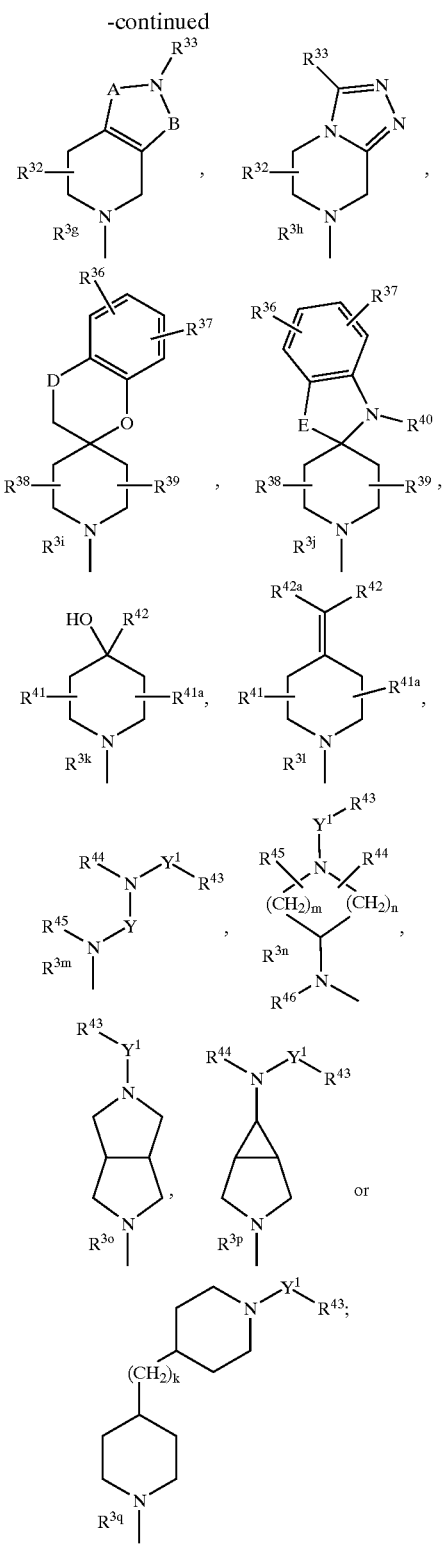

wherein said radical of formula $R^{3a}$ is additionally substituted on the ring by $R^6$, $R^7$ and $R^8$;

said radical of formula $R^{3b}$ is additionally substituted on the ring by $R^{18}$, $R^{19}$ and $R^{20}$;

G, $G^1$ and $G_2$ are taken separately and are each hydrogen and $R^6$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; $R^7$ and $R^8$ are each independently hydrogen or $(C_1-C_4)$alkyl; or G and $G^1$ are taken together and are $(C_1-C_3)$alkylene and $R^6$, $R^7$, $R^8$ and $G_2$ are hydrogen; or $G^1$ and $G_2$ are taken together and are $(C_1-C_3)$alkylene and $R^6$, $R^7$, $R^8$ and G are hydrogen;

q is 0 or 1;

X is a covalent bond, —(C=NR$^{10}$)—, oxycarbonyl, vinylenylcarbonyl, oxy$(C_1-C_4)$alkylenylcarbonyl, $(C_1-C_4)$alkylenylcarbonyl, $(C_3-C_4)$alkenylcarbonyl, thio$(C_1-C_4)$alkylenylcarbonyl, vinylenylsulfonyl, sulfinyl-$(C_1-C_4)$alkylenylcarbonyl, sulfonyl-$(C_1-C_4)$alkylenylcarbonyl or carbonyl$(C_0-C_4)$alkylenylcarbonyl; wherein said oxy$(C_1-C_4)$alkylenylcarbonyl, $(C_1-C_4)$alkylenylcarbonyl, $(C_3-C_4)$alkenylcarbonyl and thio$(C_1-C_4)$alkylenylcarbonyl in the definition of X are each optionally and independently substituted with up to two $(C_1-C_4)$alkyl, benzyl or Ar; said vinylenylsulfonyl and said vinylenylcarbonyl in the definition of X are optionally substituted independently on one or two vinylenyl carbons with $(C_1-C_4)$alkyl, benzyl or Ar; and said carbonyl$(C_0-C_4)$alkylenylcarbonyl in the definition of X is optionally substituted indepedently with up to three $(C_1-C_4)$alkyl, benzyl or Ar;

$R^{10}$ is hydrogen or $(C_1-C_4)$alkyl;

$R^9$ is $(C_3-C_7)$cycloalkyl, Ar$^1$—$(C_0-C_3)$alkylenyl or $(C_1-C_6)$alkyl optionally substituted with up to five fluoro; provided that when q=0 and X is a covalent bond, oxycarbonyl or $(C_1-C_4)$alkylenylcarbonyl, then $R^9$ is not $(C_1-C_6)$alkyl;

Ar and Ar$^1$ are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur;

Ar and Ar$^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from $R^{11}$, $R^{12}$, $R^{13}$ and $R^{14}$; wherein $R^{11}$, $R^{12}$, $R^{13}$ and $R^{14}$ are each taken separately and are each independently halo, formyl, $(C_1-C_6)$alkoxycarbonyl, $(C_1-C_6)$alkylenyloxycarbonyl, $(C_1-C_4)$alkoxy-$(C_1-C_4)$alkyl, C(OH)R$^{15}$R$^{16}$, naphthyl, phenyl, imidazolyl, pyridyl, triazolyl, morpholinyl, ($C_0$–$C_4$)alkylsulfamoyl, N-($C_0$–$C_4$)alkylcarbamoyl, N,N-di-($C_1$–$C_4$)alkylcarbamoyl, N-phenylcarbamoyl, N-($C_1$–$C_4$)alkyl-N-phenylcarbamoyl, N,N-diphenyl carbamoyl, ($C_1$–$C_4$)alkylcarbonylamido, ($C_3$–$C_7$) cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-($C_1$–$C_4$)alkyl-3,8-diaza[3.2.1]bicyclooctyl,3,5-dioxo-1,2,4-triazinyl, phenoxy, thiophenoxy, ($C_1$–$C_4$) alkylsulfanyl, ($C_1$–$C_4$)alkylsulfonyl, ($C_3$–$C_7$) cycloalkyl, ($C_1$–$C_4$)alkyl optionally substituted with up to five fluoro or ($C_1$–$C_4$)alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-($C_1$–$C_4$)alkyl, ($C_1$–$C_4$)alkoxy-($C_1$–$C_4$) alkyl, ($C_1$–$C_4$)alkyl optionally substituted with up to five fluoro and ($C_1$–$C_4$)alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; said morpholinyl in the definition of $R^{11}$, $R^{12}$, $R^{13}$ and $R^{14}$ is optionally substituted with up to two substituents independently selected from ($C_1$–$C_4$)alkyl; said pyrrolidinyl in the definition of $R^{11}$, $R^{12}$, $R^{13}$ and $R^{14}$ is optionally substituted with up to two substituents independently selected from hydroxy, hydroxy-($C_1$–$C_3$)alkyl, ($C_1$–$C_4$) alkoxy-($C_1$–$C_4$)alkyl, ($C_1$–$C_4$)alkyl optionally substituted with up to five fluoro and ($C_1$–$C_4$)alkoxy optionally substituted with up to five fluoro; said piperazinyl in the definition of $R^{11}$, $R^{12}$, $R^{13}$ and $R^{14}$ is optionally substituted with up to three substituents independently selected from ($C_1$–$C_4$)alkoxy-($C_1$–$C_4$)alkyl, hydroxy-($C_1$–$C_3$)alkyl, phenyl, pyridyl, ($C_0$–$C_4$)alkylsulfamoyl, ($C_1$–$C_4$)alkyl optionally substituted with up to five fluoro and ($C_1$–$C_4$)alkoxy optionally substituted with up to five fluoro; said triazolyl in the definition of $R^{11}$, $R^{12}$, $R^{13}$ and $R^{14}$ is optionally substituted with hydroxy, halo, hydroxy-($C_1$–$C_4$)alkyl, ($C_1$–$C_4$)alkoxy-($C_1$–$C_4$) alkyl, ($C_1$–$C_4$)alkyl optionally substituted with up to five fluoro and ($C_1$–$C_4$)alkoxy optionally substituted with up to five fluoro; said tetrazolyl in the definition of $R^{11}$, $R^{12}$, $R^{13}$ and $R^{14}$ is optionally substituted with hydroxy-($C_2$–$C_3$)alkyl or ($C_1$–$C_4$)alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-($C_1$–$C_4$)alkyl, ($C_1$–$C_4$)alkoxy-($C_1$–$C_4$)alkyl, ($C_1$–$C_4$) alkyl optionally substituted with up to five fluoro and ($C_1$–$C_4$)alkoxy optionally substituted with up to five fluoro; or $R^{11}$ and $R^{12}$ are taken together on adjacent carbon atoms and are —$CH_2OC(CH_3)_2OCH_2$— or —O—$(CH_2)_p$—

O—, and $R^{13}$ and $R^{14}$ are taken separately and are each independently hydrogen or ($C_1$–$C_4$)alkyl;

p is 1, 2 or 3;

$R^{15}$ and $R^{16}$ are taken separately and are each independently hydrogen, ($C_1$–$C_4$)alkyl optionally substituted with up to five fluoro; or $R^{15}$ and $R^{16}$ are taken separately and $R^{15}$ is hydrogen and $R^{16}$ is ($C_3$–$C_6$) cycloalkyl, hydroxy-($C_1$–$C_3$)alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are ($C_3$–$C_6$)alkylene;

$G^3$, $G^4$ and $G^5$ are taken separately and are each hydrogen; r is 0; $R^{18}$ is hydrogen, ($C_1$–$C_4$)alkyl, ($C_1$–$C_4$) alkoxycarbonyl, ($C_1$–$C_4$)alkoxy-($C_1$–$C_4$)alkyl, hydroxy-($C_1$–$C_4$)alkyl or phenyl optionally independently substituted with up to three hydroxy, halo, hydroxy-($C_1$–$C_4$)alkyl, ($C_1$–$C_4$)alkoxy-($C_1$–$C_4$)alkyl, ($C_1$–$C_4$)alkyl or ($C_1$–$C_4$)alkoxy, wherein said ($C_1$–$C_4$) alkyl in the definition of $R^6$ and said ($C_1$–$C_4$)alkoxy in the definition of $R^6$ are optionally and independently substituted with up to five fluoro; and $R^{19}$ and $R^{20}$ are each independently ($C_1$–$C_4$)alkyl; or $G^3$, $G^4$ and $G^5$ are taken separately and are each hydrogen; r is 1; $R^{18}$ is hydrogen, ($C_1$–$C_4$)alkyl, ($C_1$–$C_4$) alkoxycarbonyl, ($C_1$–$C_4$)alkoxy-($C_1$–$C_4$)alkyl, hydroxy-($C_1$–$C_4$)alkyl or phenyl optionally independently substituted with up to three hydroxy, halo, hydroxy-($C_1$–$C_4$)alkyl, ($C_1$–$C_4$)alkoxy-($C_1$–$C_4$)alkyl, ($C_1$–$C_4$)alkyl or ($C_1$–$C_4$)alkoxy, wherein said ($C_1$–$C_4$) alkyl in the definition of $R^6$ and said ($C_1$–$C_4$)alkoxy in the definition of $R^6$ are optionally and independently substituted with up to five fluoro; and $R^{19}$ and $R^{20}$ are each independently hydrogen or ($C_1$–$C_4$)alkyl; or $G^3$ and $G^4$ are taken together and are ($C_1$–$C_3$)alkylene; r is 0 or 1; and $R^{18}$, $R^{19}$, $R^{20}$ and $G^5$ are hydrogen; or $G^4$ and $G^5$ are taken together and are ($C_1$–$C_3$)alkylene; r is 0 or 1; and $R^{18}$, $R^{19}$, $R^{20}$ and G3 are hydrogen;

$R^{17}$ is $SO_2NR^{21}R^{22}$, $CONR^{21}R^{22}$, ($C_1$–$C_6$) alkoxycarbonyl, ($C_1$–$C_6$)alkylcarbonyl, $Ar^2$-carbonyl, ($C_1$–$C_6$)alkylsulfonyl, ($C_1$–$C_6$)alkylsulfinyl, $Ar^2$-sulfonyl, $Ar^2$-sufinyl and ($C_1$–$C_6$)alkyl;

$R^{21}$ and $R^{22}$ are taken separately and are each independently selected from hydrogen, ($C_1$–$C_6$)alkyl, ($C_3$–$C_7$) cycloalkyl and $Ar^2$—($C_0$–$C_4$)alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl,6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-($C_1$–$C_4$)alkyl, ($C_1$–$C_4$)alkoxy-($C_1$–$C_4$alkyl, ($C_1$–$C_4$) alkyl optionally substituted with up to five fluoro and ($C_1$–$C_4$)alkoxy optionally substituted with up to five fluoro; said pyrrolidinyl, piperidinyl, azepinyl in the definition of $R^{21}$ and $R^{22}$ are optionally substituted independently with up to two substituents independently selected from hydyroxy, amino, hydroxy-($C_1$–$C_4$)alkyl, ($C_1$–$C_4$)alkoxy-($C_1$–$C_4$)alkyl, ($C_1$–$C_4$) alkyl optionally substituted with up to five fluoro and ($C_1$–$C_4$)alkoxy optionally substituted with up to five fluoro; said morpholinyl in the definition of $R^{21}$ and $R^{22}$ is optionally substituted with up to two substituents independently selected from hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; said piperazinyl in the definition of $R^{21}$ and $R^{22}$ is optionally substituted independently with up to three substituents independently selected from phenyl, pyridyl, ($C_1$–$C_4$)alkoxycarbonyl and ($C_1$–$C_4$)alkyl optionally substituted with up to five fluoro; said 1,2,3,4-tetrahydroisoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro;

$Ar^2$ is independently defined as set forth for Ar and $Ar^1$ above;

said $Ar^2$ is optionally independently substituted as set forth for Ar and $Ar^1$ above;

$R^{23}$ is $CONR^{25}R^{26}$ or $SO_2R^{25}R^{26}$, wherein $R^{25}$ is hydrogen ($C_1$–$C_4$)alkyl or $Ar^3$—($C_0$–$C_4$)alkylenyl and $R^{26}$ is $Ar^3$—($C_0$–$C_4$)alkylenyl; provided that when $Ar^3$ is phenyl, naphthyl or biphenyl, then $R^{23}$ cannot be $CONR^{25}R^{26}$ where $R^{25}$ is hydrogen or $Ar^3$ and $R^{26}$ is $Ar^3$;

$R^{24}$ is hydrogen, ($C_1$–$C_4$)alkyl, ($C_1$–$C_4$)alkoxycarbonyl, ($C_1$–$C_4$)alkoxy-($C_1$–$C_4$)alkyl, hydroxy-($C_1$–$C_4$)alkyl or phenyl optionally independently substituted with up to three hydroxy, halo, hydroxy-($C_1$–$C_4$)alkyl, ($C_1$–$C_4$)alkoxy-($C_1$–$C_4$)alkyl, ($C_1$–$C_4$)alkyl or ($C_1$–$C_4$)alkoxy, wherein said ($C_1$–$C_4$)alkyl in the definition of $R^6$ and said ($C_1$–$C_4$)alkoxy in the definition of $R^6$ optionally and independently substituted with up to five fluoro;

$Ar^3$ is independently defined as set forth for Ar and $Ar^1$ above;

said $Ar^3$ is optionally independently substituted as set forth for Ar and $Ar^1$ above;

$R^{27}$ is hydrogen or ($C_1$–$C_4$)alkyl;

$R^{28}$ and $R^{29}$ are each independently hydrogen, hydroxy, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro, ($C_1$–$C_4$)alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-($C_1$–$C_4$)alkyl, ($C_1$–$C_4$)alkoxy-($C_1$–$C_4$) alkyl, ($C_1$–$C_4$)alkyl optionally substituted with up to five fluoro or ($C_1$–$C_4$)alkoxy optionally substituted with up to five fluoro;

$R^{30}$ and $R^{31}$ are each independently hydrogen, ($C_1$–$C_4$)alkyl, ($C_3$–$C_7$)cycloalkyl or phenyl, said phenyl is optionally substituted with up to three hydroxy, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; said indolinyl and piperazinyl in the definition of $R^{30}$ and $R^{31}$ are optionally substituted with up to three hydroxy, amino, hydroxy-($C_1$–$C_4$)alkyl, ($C_1$–$C_4$)alkoxy-($C_1$–$C_4$)alkyl, ($C_1$–$C_4$)alkoxycarbonyl, ($C_1$–$C_4$)alkyl optionally substituted with up to five fluoro or ($C_1$–$C_4$)alkoxy optionally substituted with up to five fluoro; said morpholinyl in the definition of $R^{30}$ and $R^{31}$ is optionally substituted with up to two substituents independently selected from hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro;

A is N optionally substituted with hydrogen or ($C_1$–$C_4$) alkyl and B is carbonyl; or A is carbonyl and B is N optionally substituted with hydrogen or ($C_1$–$C_4$)alkyl;

$R^{32}$ is hydrogen or ($C_1$–$C_4$)alkyl;

$R^{33}$ is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro;

$R^{34}$ and $R^{35}$ are each independently hydrogen, ($C_1$–$C_4$ alkyl), phenyl or phenylsulfonyl; said phenyl and phenylsulfonyl in the definition of $R^{34}$ and $R^{35}$ are optionally substituted with up to three halo, hydroxy, ($C_1$–$C_4$) alkyl optionally substituted with up to five fluoro or ($C_1$–$C_4$)alkoxy optionally substituted with up to five fluoro;

D is CO, CHOH or $CH_2$;

E is O, NH or S;

$R^{36}$ and $R^{37}$ are taken separately and are each independently hydrogen, halo, cyano, hydroxy, amino, ($C_1$–$C_6$) alkylamino, di-($C_1$–$C_6$)alkylamino, pyrrolidino, piperidino, morpholino, ($C_1$–$C_4$)alkoxy-($C_1$–$C_4$)alkyl, hydroxy-($C_1$–$C_4$)alkyl, $Ar^4$, ($C_1$–$C_4$)alkyl optionally substituted with up to five fluoro or ($C_1$–$C_4$)alkoxy optionally substituted with up to five fluoro;

$R^{38}$, $R^{39}$ and $R^{40}$ are each independently hydrogen or ($C_1$–$C_4$)-alkyl;

$Ar^4$ is phenyl, furanyl, thienyl, pyridyl, pyrimidyl, pyrazinyl or pyridazinyl; said $Ar^4$ being optionally substituted with up to three hydroxy, ($C_1$–$C_4$)alkoxy-($C_1$–$C_4$)alkyl, halo, hydroxy-($C_1$–$C_4$)alkyl, ($C_1$–$C_4$)alkyl optionally substituted with up to five fluoro or ($C_1$–$C_4$)alkoxy optionally substituted with up to five fluoro; or $R^{36}$ and $R^{37}$ are taken together on adjacent carbon atoms and are —O—($CH_2$)$_t$—O—;

t is 1, 2 or 3;

Y is ($C_2$–$C_6$)alkylene;

$R^{44}$, $R^{45}$ and $R^{46}$ are each independently hydrogen or ($C_1$–$C_4$)alkyl;

m and n are each independently 1, 2 or 3, provided that the sum of m and n is 2, 3 or 4;

k is 0, 1, 2, 3 or 4;

$Y^1$ is a covalent bond, carbonyl, sulfonyl or oxycarbonyl;

$R^{43}$ is ($C_3$–$C_7$)cycloalkyl, $Ar^5$—($C_0$–$C_4$)alkylenyl, $NR^{47}R^{48}$ or ($C_1$–$C_6$)alkyl optionally substituted with one to five fluoro; provided that when $Y^1$ is a covalent bond or oxycarbonyl, then $R^{43}$ is not $NR^{47}R^{48}$;

$R^{47}$ and $R^{48}$ are taken separately and are each independently selected from hydrogen, $Ar^5$, ($C_1$–$C_6$)alkyl and $Ar^5$—($C_0$–$C_4$)alkylenyl; or $R^{47}$ and $R^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-($C_1$–$C_4$)alkyl, ($C_1$–$C_4$)alkoxy-($C_1$–$C_4$)alkyl, ($C_1$–$C_4$) alkyl optionally substituted with up to five fluoro or ($C_1$–$C_4$)alkoxy optionally substituted with up to five fluoro; said morpholinyl in the definition of $R^{47}$ and $R^{48}$ is optionally substituted with up to two substituents independently selected from hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro;

$Ar^5$ is independently defined as set forth for Ar and $Ar^1$ above;

$Ar^5$ is optionally independently substituted as set forth for Ar and $Ar^1$ above;

$R^{42}$ and $R^{42a}$ are independently hydrogen, ($C_3$–$C_7$)cycloalkyl, $Ar^6$—($C_0$–$C_3$)alkylenyl, $Ar^6$—($C_{2–C4}$)alkenyl, $Ar^6$-carbonyl or ($C_1$–$C_6$)alkyl optionally substituted with up to five fluoro;

$Ar^6$ is independently defined as set forth for Ar and $Ar^1$ above;

$Ar^6$ is optionally independently substituted as set forth for Ar and $Ar^1$ above; and $R^{41}$ and $R^{41a}$ are each independently hydrogen or ($C_1$–$C_4$) alkyl.

10. A method of claim 9 wherein in said compound of Formula I, said prodrug thereof or said pharmaceutically acceptable salt of said compound or said prodrug:

$R^1$ is $C(OH)R^4R^5$, where $R^4$ and $R^5$ are each independently hydrogen or methyl;

$R^2$ is hydrogen;

$R^3$ is

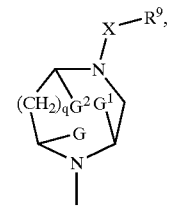

wherein said $R^3$ is substituted by $R^6$, $R^7$ or

G, $G^1$ and $G^2$ are taken separately and are each hydrogen and $R^6$ is hydrogen or ($C_1$–$C_4$)alkyl; $R^7$ and $R^8$ are each independently hydrogen or ($C_1$–$C_4$)alkyl; or G and $G^1$ are taken together and are ($C_1$–$C_3$)alkylene and $R^6$, $R^7$, $R^8$ and $G^2$ are hydrogen; or $G^1$ and $G^2$ are taken together and are ($C_1$–$C_3$)alkylene and $R^6$, $R^7$, $R^8$ and G are hydrogen;

q is 0 or 1;

X is a covalent bond, oxycarbonyl, vinylenylcarbonyl, oxy($C_1$–$C_4$)alkylenylcarbonyl, thio($C_1$–$C_4$)alkylenylcarbonyl or vinylenylsulfonyl; said vinylenylcarbonyl and said vinylenylsulfonyl in the definition of X are optionally substituted on one or two vinylenyl carbons with ($C_1$–$C_4$)alkyl, benzyl or Ar; said oxy ($C_1$–$C_4$)alkylenylcarbonyl and said thio($C_1$–$C_4$)alkylenylcarbonyl in the definition of X are optionally substituted with up to two ($C_1$–$C_4$)alkyl, benzyl or Ar;

$R^9$ is ($C_3$–$C_7$)cycloalkyl, $Ar^1$—($C_0$–$C_4$)alkylenyl or ($C_1$–$C_6$)alkyl optionally substituted with up to five fluoro;

$Ar^1$ is phenyl, naphthyl, pyridyl, pyrimidyl, pyrazinyl, pyridazinyl, triazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, th azolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; and said $Ar^1$ is optionally substituted as set forth in claim 7.

11. A method of claim 10 wherein said compound of Formula I is
1R-(4-{1'-[2-(1R-hydroxy-ethyl)-pyrimidin-4-yl]-[4,4']bipiperidinyl-1-yl}-pyrimidin-2-yl)-ethanol;
furo[3,2-c]pyridin-2-yl-{4-[2-(1R-hydroxy-ethyl)-pyrimidin-4-yl]-3R,5S-dimethyl-piperazin-1-yl}-methanone;
(4-chloro-furo[3,2-c]pyridin-2-yl)-{4-[2-(1R-hydroxy-ethyl)-pyrimidin-4-yl]-3R,5S-dimethyl-piperazin-1-yl}-methanone;
{4-[2-(1R-hydroxy-ethyl)-pyrimidin-4-yl]-3R,5S-dimethyl-piperazin-1-yl}-(4-pyrrolidin-1-yl-furo[3,2-c]pyridin-2-yl)-methanone;
{4-[2-(1R-hydroxy-ethyl)-pyrimidin-4-yl]-3R,5S-dimethyl-piperazin-1-yl}-(4-morpholin-4-yl-furo[3,2-c]pyridin-2-yl)-methanone;
{4-[2-(1R-hydroxy-ethyl)-pyrimidin-4-yl]-3R,5S-dimethyl-piperazin-1-yl}-imidazo[1,2-a]pyridin-2-yl-methanone;
furo[3,2-c]pyridin-2-yl-{4-[2-(1R-hydroxy-ethyl)-pyrimidin-4-yl]-2R,6S-dimethyl-piperazin-1-yl}-methanone;
4-[2-(1R-hydroxy-ethyl)-pyrimidin-4-yl]-2R,6S-dimethyl-piperazine-1-carboxylic acid pyridin-3-yl ester;
4-[2-(1R-hydroxy-ethyl)-pyrimidin-4-yl]-2R,6S-dimethyl-piperazine-1-carboxylic acid 2-methyl-pyridin-3-yl ester;
4-[2-(1R-hydroxy-ethyl)-pyrimidin-4-yl]-2R,6S-dimethyl-piperazine-1-carboxylic acid 5-chloro-pyridin-3-yl ester;
4-[2-(1R-hydroxy-ethyl)-pyrimidin-4-yl]-2R,6S-dimethyl-piperazine-1-carboxylic acid 6-methyl-pyridin-3-yl ester;
(E)-1-{4-[2-(1R-hydroxy-ethyl)-pyrimidin-4-yl]-2R,6S-dimethyl-piperazin-1-yl}-3-thiophen-2-yl-propenone;
1R-{4-[4-(4,6-dimethyl-pyrimidin-2-yl)-3R,5S-dimethyl-piperazin-1-yl]-pyrimidin-2-yl}-ethanol;
1R-{4-[4-(4-methoxymethyl-6-methyl-pyrimidin-2-yl)-3R,5S-dimethyl-piperazin-1-yl]-pyrimidin-2-yl}-ethanol;
1R-{4-[4-(4-hydroxymethyl-6-methyl-pyrimidin-2-yl)-3R,5S-dimethyl-piperazin-1-yl]-pyrimidin-2-yl}-ethanol;
1R-(4-{3R,5S-dimethyl-4-[2-(4-methyl-piperazin-1-yl)-pyrimidin-4-yl]-piperazin-1-yl}-pyrimidin-2-yl)-ethanol;
1R-(4-{4-[2-(4-ethyl-piperazin-1-yl)-pyrimidin-4-yl]-3R,5S-dimethyl-piperazin-1-yl}-pyrimidin-2-yl)-ethanol;
1R-(4-{3R,5S-dimethyl-4-[2-(4-methyl-imidazol-1-yl)-pyrimidin-4-yl]-piperazin-1-yl}-pyrimidin-2-yl)-ethanol;
1R-(4-{3R,5S-dimethyl-4-[2-(2-methyl-imidazol-1-yl)-pyrimidin-4-yl]-piperazin-1-yl}-pyrimidin-2-yl)-ethanol;
1R-(4-{4-[2-(2,4-dimethyl-imidazol-1-yl)-pyrimidin-4-yl]-3R,5S-dimethyl-piperazin-1-yl}-pyrimidin-2-yl)-ethanol;
1R-(4-{4-[2-(4-isopropyl-piperazin-1-yl)-pyrimidin-4-yl]-3R,5S-dimethyl-piperazin-1-yl}-pyrimidin-2-yl)-ethanol;
1R-(4-{3R,5S-dimethyl-4-[4-methyl-6-(4-methyl-piperazin-1-yl)-[1,3,5]triazin-2-yl]-piperazin-1-yl}-pyrimidin-2-yl)-ethanol;
1R-{4-[4-(4-methoxy-6-methyl-[1,3,5]triazin-2-yl)-3R,5S-dimethyl-piperazin-1-yl]-pyrimidin-2-yl}-ethanol;
1R-{4-[4-(4,6-dimethoxy-[1,3,5]triazin-2-yl)-3R,5S-dimethyl-piperazin-1-yl]-pyrimidin-2-yl}-ethanol;
1R-{4-[4-(4-ethoxy-6-methyl-[1,3,5]triazin-2-yl)-3R,5S-dimethyl-piperazin-1-yl]-pyrimidin-2-yl}-ethanol;
1R-{4-[4-(4-isopropoxy-6-methyl-[1,3,5]triazin-2-yl)-3R,5S-dimethyl-piperazin-1-yl]-pyrimidin-2-yl}-ethanol;
1R-{4-[3R,5S-dimethyl-4-(4-phenyl-[1,3,5]triazin-2-yl)-piperazin-1-yl]-pyrimidin-2-yl}-ethanol;
1R-{4-[4-(4-hydroxymethyl-6-methoxy-[1,3,5]triazin-2-yl)-3R,5S-dimethyl-piperazin-1-yl]-pyrimidin-2-yl}-ethanol;
1R-{4-[4-(4-isopropoxy-6-methoxy-[1,3,5]triazin-2-yl)-3R,5S-dimethyl-piperazin-1-yl]-pyrimidin-2-yl}-ethanol;
1R-{4-[4-(4-isopropyl-[1,3,5]triazin-2-yl)-3R,5S-dimethyl-piperazin-1-yl]-pyrimidin-2-yl}-ethanol;
1R-{4-[4-(4-ethyl-6-methoxy-[1,3,5]triazin-2-yl)-3R,5S-dimethyl-piperazin-1-yl]-pyrimidin-2-yl}-ethanol;
1R-{4-[4-(4,6-dimethyl-pyrimidin-2-yl)-2R,6S-dimethyl-piperazin-1-yl]-pyrimidin-2-yl}-ethanol;
1R-{4-[4-(4-hydroxymethyl-6-methyl-pyrimidin-2-yl)-2R,6S-dimethyl-piperazin-1-yl]-pyrimidin-2-yl}-ethanol;
1R-{4-[2R,6S-dimethyl-4-(4-[1,2,4]triazol-1-yl-pyrimidin-2-yl)-piperazin-1-yl]-pyrimidin-2-yl}-ethanol;
1R-{4-[4-(2,6-dimethyl-pyrimidin-4-yl)-2R,6S-dimethyl-piperazin-1-yl]-pyrimidin-2-yl}-ethanol;
1R-(4-{4-[2-(1R-hydroxy-ethyl)-pyrimidin-4-yl]-2R,6S-dimethyl-piperazin-1-yl}-pyrimidin-2-yl)-ethanol;
1R-{4-[4-(2-hydroxymethyl-6-methyl-pyrimidin-4-yl)-2R,6S-dimethyl-piperazin-1-yl]-pyrimidin-2-yl}-ethanol;
1R-(4-{4-[2-(1S-hydroxy-ethyl)-pyrimidin-4-yl]-2R,6S-dimethyl-piperazin-1-yl}-pyrimidin-2-yl)-ethanol;
1S-(4-{4-[2-(1R-hydroxy-ethyl)-pyrimidin-4-yl]-2R,6S-dimethyl-piperazin-1-yl}-pyrimidin-2-yl)-ethanol;
1-{4-[4-(2-acetyl-pyrimidin-4-yl)-2R,6S-dimethyl-piperazin-1-yl]-pyrimidin-2-yl}-ethanone;
1RS-(4-{4-[2-(1RS-hydroxy-ethyl)-pyrimidin-4-yl]-2R,6S-dimethyl-piperazin-1-yl}-pyrimidin-2-yl)-ethanol;
(4-{4-[2-(1R-hydroxy-ethyl)-pyrimidin-4-yl]-3R,5S-dimethyl-piperazin-1-yl}-pyrimidin-2-yl)-ethanone;
1R-{4-[2R,6S-dimethyl-4-(2-morpholin-4-yl-pyrimidin-4-yl)-piperazin-1-yl]-pyrimidin-2-yl}-ethanol;
1R-(4-{2R,6S-dimethyl-4-[2-(4-methyl-piperazin-1-yl)-pyrimidin-4-yl]-piperazin-1-yl}-pyrimidin-2-yl)-ethanol;
1R-{4-[2R,6S-dimethyl-4-(2-[1,2,4]triazol-1-yl-pyrimidin-4-yl)-piperazin-1-yl]-pyrimidin-2-yl}-ethanol;
1R-(4-{[2-(1R-hydroxy-ethyl)-pyrimidin-4-yl]-2R,6R-dimethyl-piperazin-1-yl}-pyrimidin-2-yl)-ethanol;
1R-(4-{4-[2-(4-ethyl-piperazin-1-yl)-pyrimidin-4-yl]-2R,6S-dimethyl-piperazin-1-yl}-pyrimidin-2-yl)-ethanol;
1R-(4-{2R,6S-dimethyl-4-[2-(4-methyl-imidazol-1-yl)-pyrimidin-4-yl]-piperazin-1-yl}-pyrimidin-2-yl)-ethanol;
1R-(4-{4-[2-(2,4-dimethyl-imidazol-1-yl)-pyrimidin-4-yl]-2R,6S-dimethyl-piperazin-1-yl}-pyrimidin-2-yl)-ethanol;
1R-{4-[2R,6S-dimethyl-4-(4-morpholin-4-yl-[1,3,5]triazin-2-yl)-piperazin-1-yl]-pyrimidin-2-yl}-ethanol;
1R-{4-[4-(4-methoxy-6-methyl-[1,3,5]triazin-2-yl)-2R,6S-dimethyl-piperazin-1-yl]-pyrimidin-2-yl}-ethanol;
1R-{4-[4-(4,6-dimethoxy-[1,3,5]triazin-2-yl)-2R,6S-dimethyl-piperazin-1-yl]-pyrimidin-2-yl}-ethanol;
1R-{4-[2R,6S-dimethyl-4-(4-phenyl-[1,3,5]triazin-2-yl)-piperazin-1-yl]-pyrimidin-2-yl}-ethanol;
1R-{4-[4-(4-hydroxymethyl-6-methyl-pyrimidin-2-yl)-3S-methyl-piperazin-1-yl]-pyrimidin-2-yl}-ethanol;
1R-{4-[4-(2-hydroxymethyl-pyrimidin-4-yl)-3S-methyl-piperazin-1-yl]-pyrimidin-2-yl}-ethanol;
1R-{4-[4-(2-hydroxymethyl-6-methyl-pyrimidin-4-yl)-3S-methyl-piperazin-1-yl]-pyrimidin-2-yl}-ethanol;
1R-[4-(3S-methyl-4-oxazolo[5,4-b]pyridin-2-yl-piperazin-1-yl)-pyrimidin-2-yl]-ethanol;

1R-[4-(3S-methyl-4-oxazolo[4,5-b]pyridin-2-yl-piperazin-1-yl)-pyrimidin-2-yl]-ethanol;
1R-[4-(3S-methyl-4-quinoxalin-2-yl-piperazin-1-yl)-pyrimidin-2-yl]-ethanol;
1R-{4-[4-(4,6-dimethyl-[1,3,5]triazin-2-yl)-3R,5S-dimethyl-piperazin-1-yl]-pyrimidin-2-yl}-ethanol;
1R-{4-[3R,5S-dimethyl-4-(4-methyl-6-phenyl-[1,3,5]triazin-2-yl)-piperazin-1-yl]pyrimidin-2-yl}-ethanol;
1R-{4-[4-(4-cyclopropyl-[1,3,5]triazin-2-yl)-3R,5S-dimethyl-piperazin-1-yl]-pyrimidin-2-yl}-ethanol;
1R-{4-[4-(4-cyclopropyl-[1,3,5]triazin-2-yl)-2R,6S-dimethyl-piperazin-1-yl]-pyrimidin-2-yl}-ethanol;
1R-{4-[4-(4,6-dimethyl-[1,3,5]triazin-2-yl)-2R,6S-dimethyl-piperazin-1-yl]-pyrimidin-2-yl}-ethanol;
1R-{4-[4-(4-hydroxymethyl-6-phenyl-[1,3,5]triazin-2-yl)-2R,6S-dimethyl-piperazin-1-yl]-pyrimidin-2-yl}-ethanol;
1R-{4-[4-(4-methoxy-6-methoxymethyl-[1,3,5]triazin-2-yl)-2R,6S-dimethyl-piperazin-1-yl]-pyrimidin-2-yl}-ethanol;
1R-{4-[2R,6S-dimethyl-4-(4-methyl-[1,3,5]triazin-2-yl)-piperazin-1-yl]-pyrimidin-2-yl-ethanol;
1-{4-[4-(2-acetyl-pyrimidin-4-yl)-2R*,6S*-dimethyl-piperazin-1-yl]-pyrimidin-2-yl}-ethanone;
1-(-4-{4-[2-(1R-hydroxy-ethyl)-pyrimidin-4-yl]-2R,6S-dimethyl-piperazin-1-yl}-pyrimidin-2-yl)-ethanone;
1R-{4-[4-(4-methoxymethyl-6-phenyl-[1,3,5]-triazin-2-yl)-2R,6S-dimethyl-piperazin-1-yl]-pyrimidin-2-yl}-ethanol;
(4-{4-[2-(1R-hydroxy-ethyl)-pyrimidin-4-yl]-2R,5S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol, a prodrug thereof or a pharmaceutically acceptable salt of said compound or said prodrug.

12. A method of claim 11 wherein said compound of Formula I is 1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-(4-{4-[2-(1S-hydroxy-ethyl)-pyrimidin-4-yl]-2R,6S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; 1-{4-[4-(2-acetyl-pyrimidin-4-yl)-2R,6S-dimethyl-piperazin-1-yl]-pyrimidin-2-yl}-ethanone; 1RS-(4-{4-[2-(1RS-hydroxy-ethyl)-pyrimidin-4-yl]-2R,6S-dimethyl-piperazin-1-yl}-pyrimidin-2-yl)-ethanol; (4-{4-[2-(1R-hydroxy-ethyl)-pyrimidin-4-yl]-3R,5S-d methyl-piperazin-1-yl}-pyrimidin-2-yl)-ethanone; 1R-{4-[2R,6S-dimethyl-4-(2-morpholin-4-yl-pyrimidin-4-yl)-piperazin-1-yl]-pyrimidin-2-yl}-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-{4-[2R,6S-dimethyl-4-(2-[1,2,4]triazol-1-yl-pyrimidin-4-yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; 1R-{4-[4-(4-cyclopropyl-[1,3,5]triazin-2-yl)-2R,6S-dimethyl-piperazin-1-yl]-pyrimidin-2-yl}-ethanol; 1R-{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-piperazin-1-yl]-pyrimidin-2-yl-ethanol; or 1R-(4-{4-[2-(2,4-dimethyl-imidazol-1-yl)-pyrimidin-4-yl]-2R,6S-dimethyl-piperazin-1-yl}-pyrimidin-2-yl)-ethanol, a prodrug thereof or a pharmaceutically acceptable salt of said compound or said prodrug.

13. A method of claim 1 wherein said GABA agonist is muscimol, progabide, riluzole, baclofen, gabapentin, vigabatrin, valproic acid, tiagabine, lamotrigine, pregabalin, phenytoin, carbamzaepine, topiramate, a prodrug thereof or a pharmaceutically acceptable salt of said GABA agonist or said prodrug and said SDI is 1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-(4-{4-[2-(1S-hydroxy-ethyl)-pyrimidin-4-yl]-2R,6S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; 1-{4-[4-(2-acetyl-pyrimidin-4-yl)-2R,6S-dimethyl-piperazin-1-yl]-pyrimidin-2-yl}-ethanone; 1RS-(4-{4-[2-(1RS-hydroxy-ethyl)-pyrimidin-4-yl]-2R,6S-dimethyl-piperazin-1-yl}-pyrimidin-2-yl)-ethanol: (4-{4-[2-(1R-hydroxy-ethyl)-pyrimidin-4-yl]-3R,5S-dimethyl-piperazin-1-yl}-pyrimidin-2-yl)-ethanone; 1R-{4-[2R,6S-d imethyl-4-(2-morpholin-4-yl-pyrimidin-4-yl)-piperazin-1-yl]-pyrimidin-2-yl}-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-{4-[2R,6S-dimethyl-4-(2-[1,2,4]triazol-1-yl-pyrimidin-4-yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; 1R-{4-[4-(4-cyclopropyl-[1,3,5]triazin-2-yl)-2R,6S-dimethyl-piperazin-1-yl]-pyrimidin-2-yl}-ethanol; 1R-{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-Piperazin-1-yl]-pyrimidin-2-yl-ethanol; or 1R-(4-{4-[2-(2,4-dimethyl-imidazol-1-yl)-pyrimidin-4-yl]-2R,6S-dimethyl-piperazin-1-yl}-pyrimidin-2-yl)-ethanol, a prodrug thereof or a pharmaceutically acceptable salt of said compound or said prodrug.

* * * * *